(12) United States Patent
Nishiyama et al.

(10) Patent No.: US 11,090,000 B2
(45) Date of Patent: Aug. 17, 2021

(54) INFORMATION PROVISION METHOD, INFORMATION PROCESSING SYSTEM, INFORMATION TERMINAL, AND INFORMATION PROCESSING METHOD

(71) Applicant: Panasonic Intellectual Property Management Co., Ltd., Osaka (JP)

(72) Inventors: Yukari Nishiyama, Tokyo (JP); Masahiko Tsukuda, Osaka (JP); Yasuaki Okumura, Kyoto (JP)

(73) Assignee: PANASONIC INTELLECTUAL PROPERTV MANAGEMENT CO., LTD., Osaka (JP)

( * ) Notice: Subject to any disclaimer, the term of this patent is extended or adjusted under 35 U.S.C. 154(b) by 194 days.

(21) Appl. No.: 16/581,798

(22) Filed: Sep. 25, 2019

(65) Prior Publication Data

US 2020/0015743 A1 Jan. 16, 2020

Related U.S. Application Data

(63) Continuation of application No. PCT/JP2018/021469, filed on Jun. 5, 2018.

(30) Foreign Application Priority Data

Jul. 7, 2017 (JP) .............................. JP2017-133387

(51) Int. Cl.
 *A61B 5/00* (2006.01)
(52) U.S. Cl.
 CPC .......... *A61B 5/4884* (2013.01); *A61B 5/0004* (2013.01); *A61B 5/0022* (2013.01);
 (Continued)

(58) Field of Classification Search
 CPC . A61B 2503/02; A61B 5/0004; A61B 5/0022; A61B 5/14546; A61B 5/4277;
 (Continued)

(56) References Cited

U.S. PATENT DOCUMENTS

2014/0288401 A1 9/2014 Ouwerkerk et al.
2016/0058376 A1 3/2016 Baek et al.

FOREIGN PATENT DOCUMENTS

JP 2014-191467 10/2014

OTHER PUBLICATIONS

International Search Report of PCT application No. PCT/JP2018/021469 dated Sep. 4, 2018.
(Continued)

*Primary Examiner* — Jonathan T Kuo
(74) *Attorney, Agent, or Firm* — Greenblum & Bernstein, P.L.C.

(57) ABSTRACT

In order to objectively grasp a stress state of a user and to prevent postpartum depression, biological gas information is acquired via a network, where the biological gas information indicates a concentration of heptadecane of the user and is obtained by a sensor that detects heptadecane released from a skin surface of the user. From a memory storing information including an upper limit of a normal range of the concentration of heptadecane per unit period, the information indicating the upper limit of the normal range is read out. When a frequency in the unit period with which the concentration of heptadecane of the user exceeds the upper limit of the normal range is determined to have an increasing tendency based on the biological gas information obtained during a pregnancy period of the user, the information related to stress of the user is output to an information terminal of the user.

18 Claims, 19 Drawing Sheets

(52) U.S. Cl.
CPC ............ *A61B 5/4343* (2013.01); *A61B 5/441* (2013.01); *A61B 5/6824* (2013.01)

(58) Field of Classification Search
CPC ..... A61B 5/4343; A61B 5/441; A61B 5/4884; A61B 5/6824; A61B 5/6831; A61B 5/7275; G01N 2033/4975; G01N 27/622; G01N 33/497; G16H 40/67; G16H 50/30
See application file for complete search history.

(56) References Cited

OTHER PUBLICATIONS

Japanese Cabinet Office, "White Paper on National Life (2008)", Chapter 1, Section 3, "2. Stressful Society and Modern pathology", Dec. 26, 2008 (Whole Sentence Translation).

General Conference (2013), Special Lectures, "Grasping Metal Problems of Pregnant Woman and Child Care", Keiko Yoshida, Child Health in Okinawa, vol. 41 (2014), Mar. 2014, pp. 3-8 (Whole Sentence Translation).

Extended European Search Report dated Jun. 3, 2020 for the related European Patent Application No. 18828006.9.

HEPTADECANE

DATA BASE (NIST)

FIG. 4

| | HEPTADECANE | | | |
|---|---|---|---|---|
| | DURING STRESS TASK | AFTER STRESS TASK | DURING RELAXATION TASK | AFTER RELAXATION TASK |
| No.1 | 10242 | 15961 | 11718 | 160936 |
| No.2 | 14452 | 12259 | 7577 | 40642 |
| No.3 | 13646 | 16282 | 7453 | 5478 |
| No.4 | 13316 | 13983 | 13103 | 16315 |
| No.5 | 15311 | 18963 | 7281 | 7265 |
| No.6 | 17787 | 9545 | 6163 | 7486 |
| No.7 | 39097 | 15972 | 12351 | 9901 |
| No.8 | 20000 | 18757 | 12058 | 13964 |
| No.9 | 36313 | 40233 | 10116 | 13240 |
| No.10 | 42356 | 18862 | 10492 | 104937 |
| No.11 | 12928 | 6268 | 9637 | 5608 |
| No.12 | 21687 | 16920 | 11679 | 17818 |
| No.13 | 102495 | 40083 | 7238 | 10730 |
| No.14 | 17705 | 17993 | 21452 | 15253 |
| No.15 | 64618 | 26613 | 16266 | 46749 |
| No.16 | 6570 | 5971 | 8020 | 8112 |
| No.17 | 22770 | 27184 | 18139 | 16227 |
| No.18 | 12142 | 30820 | 4881 | 13756 |
| No.19 | 24037 | 59214 | 11488 | 81148 |
| No.20 | 12476 | 100284 | 62554 | 23100 |
| AVERAGE | 25997 | 25608 | 13483 | 30933 |
| AVERAGE AFTER EXCLUSION | 25964 | 26519 | 13748 | 19599 |

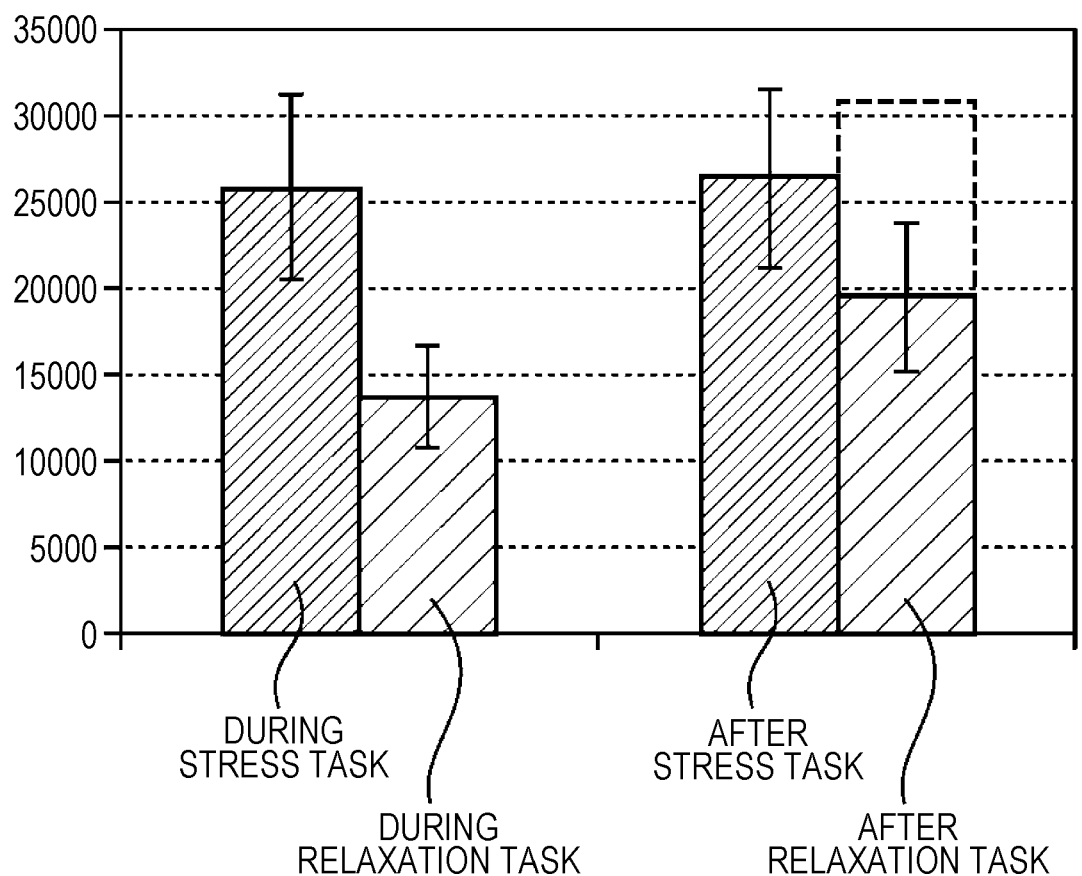

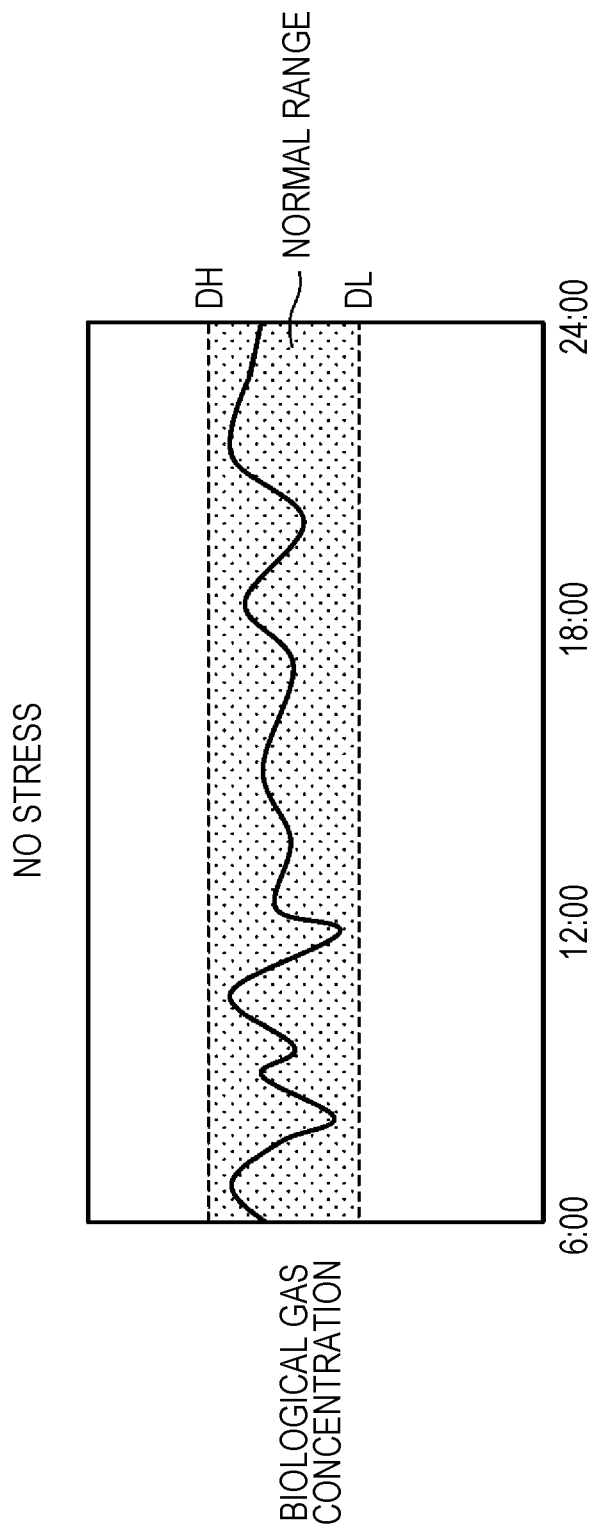

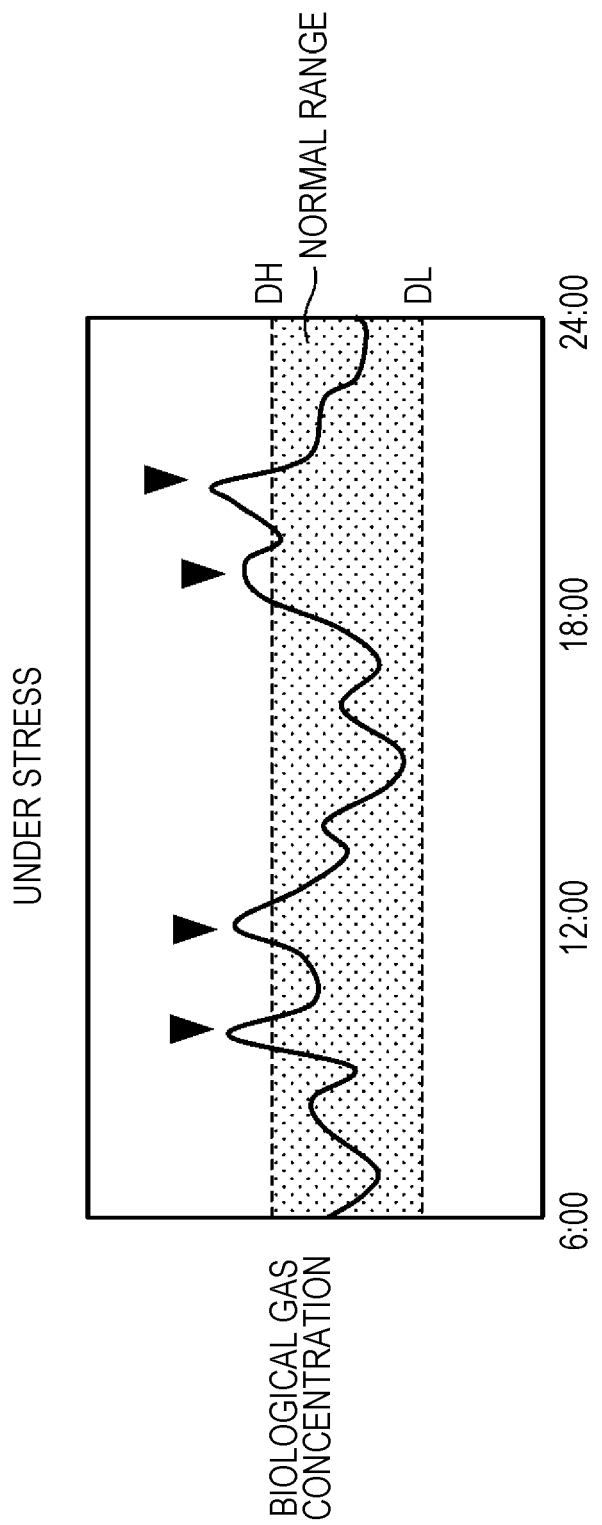

INFORMATION PROVISION METHOD, INFORMATION PROCESSING SYSTEM, INFORMATION TERMINAL, AND INFORMATION PROCESSING METHOD

TECHNICAL FIELD

The present disclosure relates to an information provision method and the like.

BACKGROUND ART

PTL 1 discloses an electronic maternal and child health handbook system that provides information by analyzing contents of items described in a Maternal and Child Health Handbook and by notifying of contents of a local government service that is desired by or suitable for the user.

In Japan, when a woman is found to be pregnant, a Maternal and Child Health Handbook is issued to the expectant woman from a local government. The expectant woman, a medical institution, and the local government write, in the Maternal and Child Health Handbook: physical conditions of the expectant woman until childbirth; physical conditions of a child at the time of or after the childbirth; being vaccinated or not; information about a growth state; and other information. The Maternal and Child Health Handbook plays a role to store record of growth. The Maternal and Child Health Handbook is a paper medium, but there is considered a computerized system of the Maternal and Child Health Handbook.

The system in PTL 1 extracts information about an expectant woman or information about a child from a data base of a computerized Maternal and Child Health Handbook and compares the extracted information with previously registered standard values. The information about the expectant woman includes a user ID, a user name, a child name, information about the expectant woman, information about the child, questions, and a content of counseling. For example, if a body weight of a one year child has gotten out of a range of an infant growth chart, the information about the child is determined to be out of a standard value. The system notifies a terminal of the user of alert information indicating that there may be a problem with the child's physical conditions and of recommendation information that recommends to have an interview with a health nurse. This operation prevents depressive symptoms, child abuses, and the like from occurring.

CITATION LIST

Patent Literature

PTL 1: Japanese Patent Application Publication No. 2014-191467

SUMMARY

Technical Problem

However, the above conventional art needs to be further improved.

Solution to Problem

An aspect of an invention according to the present disclosure is a method for providing information in an information processing system, the method comprising:

acquiring, via a network, biological gas information representing a concentration of heptadecane of a user detected with a sensor for detecting heptadecane released from a skin surface of the user;

obtaining reference information representing an upper limit of a normal range of the concentration of heptadecane per unit period of time, using a memory storing the reference information representing the upper limit of the normal range; and outputting information related to stress of the user to an information terminal after it is determined that a frequency with which the concentration of the heptadecane of the user per unit period of time is more than the upper limit of the normal range tends to increase, based on the biological gas information acquired in a pregnancy period of the user.

Advantageous Effect of Invention

The above aspect can achieve further improvement.

BRIEF DESCRIPTION OF DRAWINGS

FIG. 4 is a list of peak areas of heptadecane in the mass spectrum data by analyzing, with a gas chromatography/mass spectrometer (GC/MS), biological gases collected during a stress task, after the stress task, during a relaxation task, and after the relaxation task.

FIG. 5 is a bar chart of average values and error ranges of the peak areas of heptadecane in the list of FIG. 4.

FIG. 6A is a graph showing prediction data of biological data dealt in the first embodiment of the present disclosure.

FIG. 6B is a graph showing prediction data of the biological data dealt in the first embodiment of the present disclosure.

Figure 1:
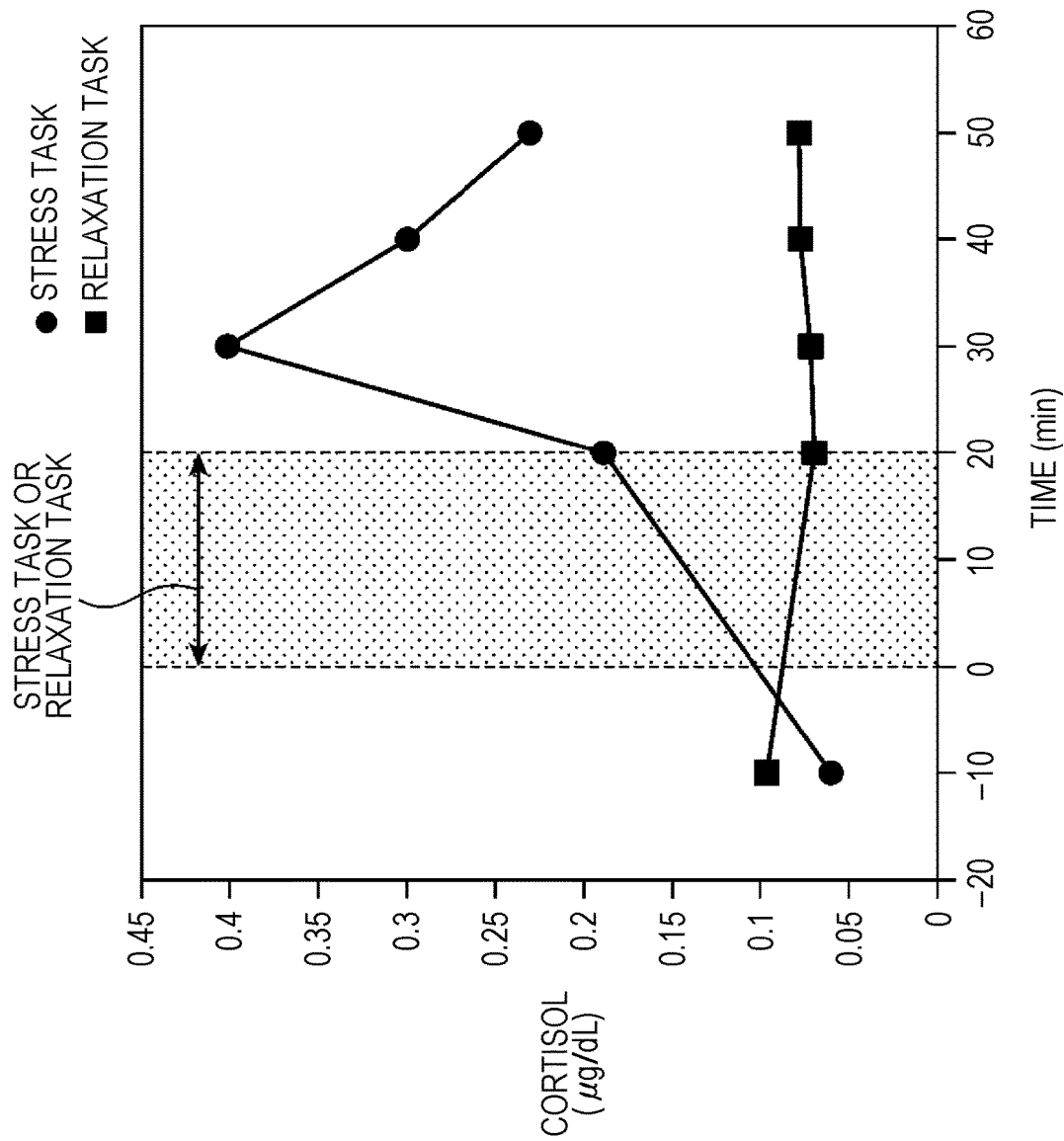
FIG. 1 is a graph showing temporal variations of concentrations of cortisol in saliva of an examinee before and after a stress task and before and after a relaxation task.

DESCRIPTION OF EMBODIMENTS (How an Aspect According to the Present Disclosure has been Conceived)

First, there will be described a point of observation of an aspect according to the present disclosure.

The present inventors have studied prevention of postpartum depression.

When postpartum depression occurs, the postpartum depression is cured by a psychiatrist. The present inventors are studying how to grasp a sign of postpartum depression and to thus prevent the postpartum depression before the postpartum depression occurs.

The present inventors have a hypothesis that there is some causation between stress and depression. Stress is not necessarily harmful to mind and body. However, when stress is accumulated, the accumulated stress tends to give adverse effects to mind and body, and depression is thought to be one of the adverse effects.

Depression is classified, depending on the cause, into three types: (1) "somatogenic depression", (2) "endogenous depression", and (3) "psychogenic depression". The "somatogenic depression" is caused by characteristics of a brain or body organ or is caused by a drug. The "endogenous depression" has a genetic-level cause or has an inherent cause in a brain that causes a mental disorder. The "psychogenic depression" is caused by experiencing psychological stress. It is difficult to strictly sort out these three causes of depression, and it is also said that there is a high possibility that the three causes interact with each other to cause depression (Cabinet Office of Japan "White Paper on the National Lifestyle 2008" Chapter 1, Section 3 "2. Stress society and modern pathology", http://www5.cao.go.jp/seikatsu/whitepaper/h20/10_pdf/01_honpen/pdf/08sh_0103_03.p df). Considering expectant women, it can be said that expectant women are under an environment where all of the above types (1) to (3) are easily satisfied. In a pregnancy period, because expectant women cannot take drugs and are restricted to exercise, it is difficult to work off stress. Therefore, there is a possibility that expectant women will develop mental disorders such as depression.

In addition, a report says that the postpartum depression tends to develop within two weeks after childbirth (Keiko Yoshida, "Understanding of mental problems with expectant women and Childcare Support" Honor lecture, General Academic meeting FY2013, The Okinawa Journal of Child Health 41 (2014): p. 3-8, http://www.osh.or.jp/in_oki/pdf/41gou/kouen.pdf). Therefore, it is important to grasp, during a pregnancy period, a sign of postpartum depression and to thus prevent postpartum depression.

In view of the above, the present inventors are studying on development of a tool for objectively grasping, before childbirth, how much stress is accumulated on an expectant woman so that postpartum depression can be prevented.

A description will be given below to cortisol, which is generally well-known in association with stress. Cortisol is hormone whose secretion amount increases when excessive stress is applied. For this reason, by examining concentration of cortisol, it is possible to grasp a stress amount at the time of the examination. The concentration of cortisol can be measured by saliva sampling, blood sampling, or urine examination. For example, if urine collection is continued for 24 hours, it is also possible to measure cumulative cortisol secretion for one day and to thus evaluate a stress amount for one day.

If concentration of cortisol is high, Cushing's syndrome, stress, depression, anorexia nervosa, and other diseases are suspected. On the other hand, if concentration of cortisol is low, Addison's disease, congenital adrenal hyperplasia, adrenocorticotropic hormone (ACTH) insensitivity, pituitary-adrenocortical insufficiency, and other diseases are suspected.

As described above, the concentration of cortisol is effective to evaluate stress, but it is not realistic to continuously perform saliva sampling, blood sampling, or urine examination. Therefore, it is difficult to grasp a temporal variation of the above concentration of cortisol. Therefore, it is also difficult to grasp a temporal variation of stress of an examinee.

To address this issue, the present inventors set up a hypothesis that, as an evaluation index replacing the above cortisol, there is a biological gas that is released from a skin surface of a person when stress is applied to mind and body. To prove the hypothesis through an experiment, the present inventors conducted an experiment to identify a biological gas that has a correlation with stress.

Specifically, the present inventors made each of 30 examinees perform a task that made each examinee feel stress, and biological gases were collected, in a specific period before and after performing the task, from an underarm and a hand of each examinee while saliva was collected from each examinee with predetermined time intervals. Then, from the saliva collected as described above, the present inventors draw graphs of temporal variations of the cortisol concentration to specify examinees whose temporal variations of the cortisol concentration were remarkable. The examinees specified above were identified to have had felt stress with the above task.

Next, the present inventors selected a plurality of biological gases that seemed to have a correlation with stress, by analyzing about 300 types of biological gases collected from the armpits of the examinees who felt stress in the above experiment. With respect to the thus selected biological gases, by checking the amounts of the biological gases during and after performing the task, it was found that heptadecane was released from skins when the examinees felt stress. The description below will show in detail a procedure of the experiment until the above heptadecane was identified.

First, the present inventors built a psychology laboratory. The psychology laboratory had inside a small isolated room. The isolated room had only a glass window, through which it is possible to observe inside from outside. In addition, the isolated room was designed so that psychological pressure was applied to an examinee when the examinee did a stress task.

The present inventors introduced 30 examinees of Japanese women in their 20's to 40's into the above psychology laboratory, one examinee at a time. Then, the saliva of the examinee was collected in the psychology laboratory. In ten minutes after the saliva of the examinee was collected, the examinee worked on a stress task including computational problems and a speech for 20 minutes. In 30 minutes just after the end of the above stress task, the saliva of the examinee was collected totally four times, once in every 10 minutes. With respect to the thus collected saliva, the concentration of cortisol in each saliva sample was measured by using a salivary cortisol quantitative kit (Salimetrics, LLC.).

In addition, along with the above saliva sampling, biological gases were collected from two places of the hand and the armpit of the examinee for 20 minutes during the stress task and for 20 minutes from 10 minutes to 30 minutes after the end of the stress task. The collection of biological gases from a hand were performed as follows: the hand of an examinee was wrapped with a bag for sampling gases and was fixed with a rubber band at a wrist part; and an absorbent for absorbing biological gases was put in the bag. The collection of biological gases from an armpit was performed by putting an absorbent under the armpit of an examinee. The absorbent put under the armpit was wrapped with cotton and was fixed with a bandage so that the absorbent could not be displaced under the armpit. The reason why biological gases were collected from the hand and the underarm was that the hand and an underarm had high density of sweat glands. Biological gases may be collected not only from the above hand and underarm but also from any parts, as long as the biological gases are collected from a skin surface.

On a day other than the day when the above stress task was performed, the saliva and the biological gases of the examinees were each collected in the same procedure as on the day when the above stress task was performed except that a relaxation task was performed instead of the stress task. As the relaxation task in the experiment, each examinee only watched a natural scenery digital versatile disc (DVD).

FIG. 1 is a graph showing temporal variations of concentrations of cortisol in saliva of an examinee before and after the stress task and before and after the relaxation task. The vertical axis represents the concentration of cortisol (μg/dL), and the horizontal axis represents the time (minute) after the start of the stress task or the relaxation task. The higher side of the vertical axis of FIG. 1 represents the higher concentration of cortisol, and the higher concentration of cortisol represents that an examinee felt the higher stress as above-mentioned. The shadowed part of the graph of FIG. 1 (from 0 minutes to 20 minutes on the horizontal axis) is a period during which the stress task or the relaxation task was performed. As a known fact, it is known that, in about 15 minutes after an examinee feels stress, the concentration of cortisol in saliva will increase.

With reference to the graph of FIG. 1, the concentration of cortisol increased rapidly at 20 minutes after the stress task was started (that is, immediately after the stress task was ended); however, there is almost no change in the concentration of cortisol between before and after the relaxation task. From this fact, it can be considered that the examinee whose concentration of cortisol showed the temporal variation of FIG. 1 felt stress with the stress task.

On the other hand, there was an examinee whose concentration of cortisol did not show such a temporal variation as that of FIG. 1. It can be considered that because such an examinee did not feel stress with the stress task, cortisol was not secreted in the saliva. Even if the biological gases of the examinee who did not feel stress as described above are evaluated, it is impossible to grasp the causation between stress and biological gases. Therefore, the examinees who did not feel stress were excluded from evaluation objects of biological gases. In this way, from the 30 examinees, there were identified top 20 examinees (examinee Nos. 1 to 20) whose concentration of cortisol remarkably increased before and after the stress task.

Figure 2:
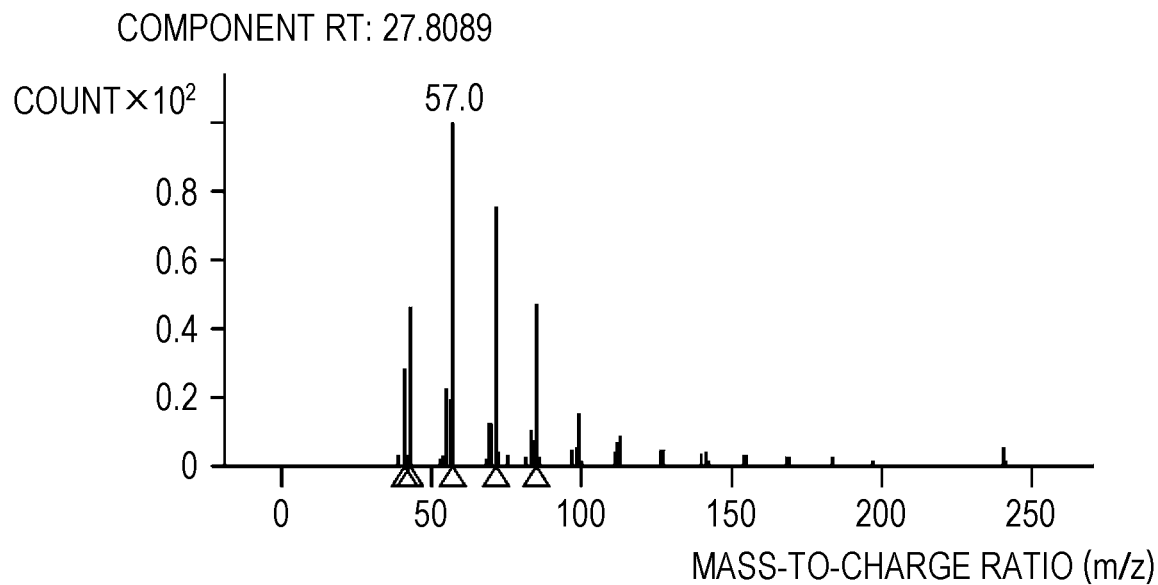
FIG. 2 is a mass spectrum data of heptadecane collected from an armpit of the examinee.
Figure 3:
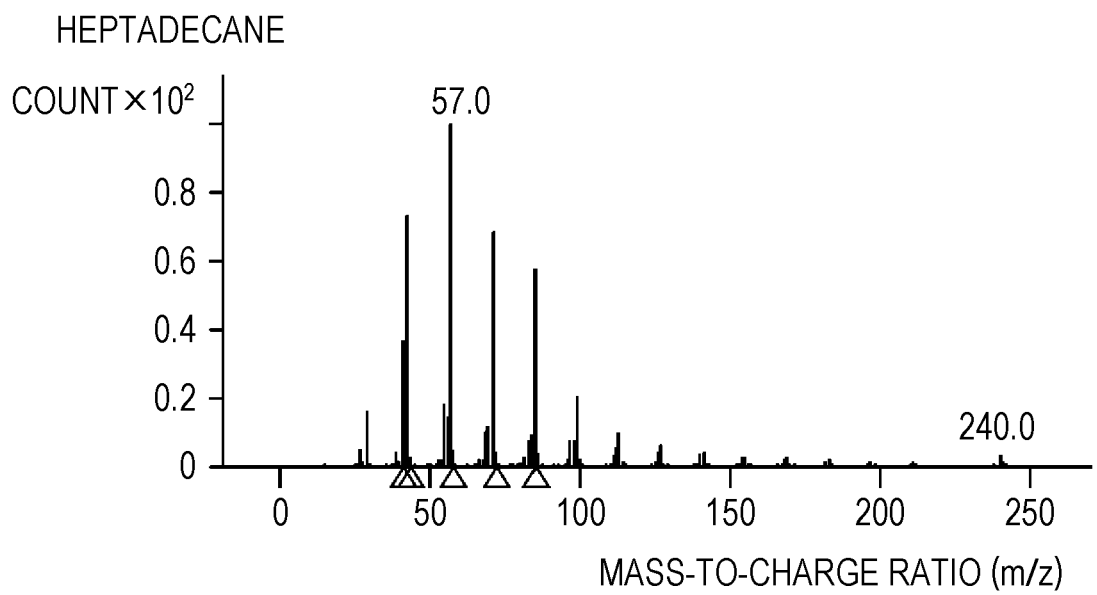
FIG. 3 is a mass spectrum data of heptadecane in the National Institute of Standards and Technology (NIST) data base.

By heating the absorbents (during the stress task, after the stress task, during the relaxation task, and after the relaxation task) collected from the armpit of each of the above identified examinees, the biological gases of each examinee absorbed in each absorbent were desorbed. By analyzing the above desorbed biological gases with a gas chromatography-mass spectrometer (GC/MS manufactured by Agilent Technologies Japan, Ltd.), mass spectrum data of the biological gases were obtained. By comparing these mass spectrum data with National Institute of Standards and Technology (NIST) data base by using Agilent Technologies' software, heptadecane was identified. FIG. 2 shows the mass spectrum data of heptadecane in the biological gas, and FIG. 3 shows the mass spectrum data of heptadecane in the NIST data base. When the mass spectra of FIG. 2 and FIG. 3 are compared with each other, similar spectrum peaks were observed at almost identical mass-to-charge ratios (m/z). As described above, it was identified that heptadecane is contained as a biological gas.

Next, with respect to the above 20 examinees, the present inventors calculated a peak area of each of the biological gases released from the underarm of each examinee (Examinee Nos. 1 to 20) during and after the stress task and during and after the relaxation task; and by comparing the peak area of a mass spectrum of each biological gas between during and after the stress task and between during and after the relaxation task, a plurality of substances were chosen as candidates related to stress from more than 300 of biological gas components. Of these candidate substances, heptadecane was apparently confirmed to have a correlation with stress. The chemical formula of heptadecane is shown below.

[Chemical formula 1]

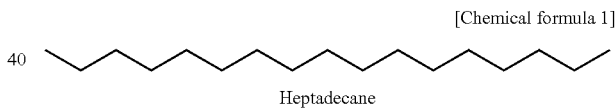

Heptadecane

Next, in the above-mentioned conditions, the peak areas of heptadecane were calculated from the mass spectra obtained with GC/MS. The table shown in FIG. 4 is a list of peak areas of heptadecane in the mass spectra obtained by analyzing, with the gas chromatography/mass spectrometry (GC/MS), the biological gases released from the underarm of each examinee (Examinee Nos. 1 to 20) during the stress task, after the stress task, during the relaxation task, and after the relaxation task. The larger value of the peak area in the mass spectrum shown in FIG. 4 indicates that the larger amount of heptadecane was released from the armpit. However, the peak areas of heptadecane after the relaxation task of the examinees Nos. 1 and 10 in the table of FIG. 4 indicated extremely larger values than the values of the other subjects, so that the measurement values of the examinees Nos. 1 and 10 were excluded as error data. The values shown in the row of "average after exclusion" in the list of FIG. 4 are average values of the peak areas of heptadecane for each of the 18 subjects in which the measurement values of the examinees Nos. 1 and 10 have been excluded. FIG. 5 is a bar chart of average values and error ranges of the peak areas of heptadecane obtained from the list of FIG. 4. For reference, in the graph of FIG. 5, an average value of the peak areas of heptadecane in which the measurement values of the examinees Nos. 1 and 10 are included (namely, that of all of the examinees Nos. 1-20) is indicated by a dot line.

With reference to FIG. 4 and FIG. 5, when the peak areas of heptadecane for the stress task were compared with the peak areas of heptadecane for the relaxation task, the peak areas of heptadecane were larger for the stress condition than for the relaxation condition.

From the above results, it has become clear that a larger amount of heptadecane was released from the underarms of the examinees during the stress task than during the relaxation task. From these results, it can be said that the release amount of heptadecane has a correlation with the stress of the examinees. Therefore, heptadecane can be an index for objectively evaluating the stress amount of an examinee. In the recognition of the present inventors, there is no case such as a paper in which the selected heptadecane has been studied in connection with stress, prior to the present application.

Next, a device to detect heptadecane was developed; thus, the device has successfully achieved objective evaluation of stress, which had been subjectively felt. That is, by using a method in which a device such as a sensor is used to measure heptadecane released from the skin surface of a human, continuous measurement can be done. In this case, it is possible to grasp when on a day a stress reaction occurred and what the person was doing when the stress reaction occurred. Thus, it is possible to objectively grasp a temporal variation of stress, and it is thus expected that stress can be controlled.

In addition, the present inventors have to lead achievement that stress can be objectively grasped by measuring the biological gas resulting from stress, to a final goal of preventing postpartum depression. Each aspect of the invention according to the present disclosure relates to how to achieve the final goal.

Based on novel knowledge obtained as a result of the present inventors' hard studying, the present inventors have conceived the invention according to the following aspects.

An aspect of the invention according to the present disclosure is a method for providing information in an information processing system, the method comprising:

acquiring, via a network, biological gas information representing a concentration of heptadecane of a user detected with a sensor for detecting heptadecane released from a skin surface of the user;

obtaining reference information representing an upper limit of a normal range of the concentration of heptadecane per unit period of time, using a memory storing the reference information representing the upper limit of the normal range; and outputting information related to stress of the user to an information terminal after it is determined that a frequency with which the concentration of the heptadecane of the user per unit period of time is more than the upper limit of the normal range tends to increase, based on the biological gas information acquired in a pregnancy period of the user.

PTL 1 uses information in a Maternal and Child Health Handbook. The information in a Maternal and Child Health Handbook is subjectively written by an expectant woman, doctors, health nurses of a local government, and others, and cannot be objective materials for decision. For example, there is a possibility that an expectant woman writes that she does not feel stress even if she receives stress. Similarly, there is a possibility that she writes that she feels great stress even if she does not receive stress. Further, it can be thought that, for example, in an environment where an expectant woman is constantly receiving stress, she may be less sensitive to stress.

In contrast, in the present aspect, a stress amount is objectively determined by using heptadecane, which is a biological gas that is supposed to have a relationship with stress. Therefore, it is possible to objectively grasp a sign of postpartum depression without being affected by the subjective view of the expectant woman.

As a result, if it is determined that a frequency in the unit period with which the concentration of heptadecane of the user exceeds the upper limit of the normal values has an increasing tendency, the information related to stress of the user is output to an information terminal. This enables the expectant woman herself to objectively know, during a pregnancy period, a sign of postpartum depression, and it can be therefore expected to prevent postpartum depression.

Note that the term "pregnancy period" means a period from the first day of the last menstruation to childbirth (delivery). However, there is a report that says that postpartum depression tends to develop within two weeks after childbirth, and a termination time of the "pregnancy period" may be set at two weeks after a childbirth in the present specification.

In addition, in the present aspect, the information including the upper limit of the normal range of the concentration of heptadecane per the unit period may be set for the user as individual information of the user, based on the biological gas information acquired in in a predetermined period in an early stage of the pregnancy period of the user.

In this case, the data of the user herself is used as a standard value. A release amount of heptadecane, which is a biological gas, is affected by age, foods, body weight, and the like and has an individual variability; therefore, it is preferable to use the data of the user herself for accurate determination.

In contrast, in PTL 1, a standard value common for all users is used.

With the present aspect, the data of the user herself is used as a standard value to determine a sign of postpartum depression. Therefore, an appropriate determination is possible for each expectant woman.

In addition, in the present aspect, the information including the upper limit of the normal range of the concentration of heptadecane per unit period may be used commonly to a plurality of users including the user.

In this case, since the standard value is commonly used for the plurality of users, it is possible to omit time and effort for generating and managing the standard value for each user.

In addition, in the present aspect, when it is not determined that the frequency with which the concentration of the heptadecane of the user per unit period of time is more than the upper limit of the normal range tends to increase, the information related to stress of the user does not have to be output to the information terminal.

In this case, it is possible to prevent the information related to stress from being output to the information terminal if there is no sign of postpartum depression observed.

Further, in the present aspect, the information terminal may be a first information terminal of the user.

In this case, because the information terminal is configured with the first information terminal of the user, if there is a sign of postpartum depression observed during a pregnancy period, an expectant woman herself can objectively know the fact, and prevention of postpartum depression can be expected.

Further, in the present aspect, the information terminal may be a second information terminal, of a consulting business operator, other than the first information terminal of the user.

In this case, because the information terminal is configured with the second information terminal of the consulting business operator, if there is a sign of postpartum depression observed during a pregnancy period, the consulting business operator can be made to objectively know the fact and can be made to take a measure, for example, to take care of the expectant woman. As a result, prevention of postpartum depression can be expected.

Further, in the present aspect, the information terminal may be a first information terminal of the user. The method may further include:

acquiring first address information on the first information terminal and second address information on the consulting business operator from a memory storing the first address information and the second address information, when it is determined that the frequency that the concentration of heptadecane of the user per the unit period of time is more than the upper limit of the normal range tends to increase; and outputting the information related to stress of the user to both of the first information terminal and a second information terminal of the consulting business operator, based on the first address information and the second address information, wherein the second information terminal of the consulting business operator is distinct from the first information terminal.

In this case, if there is a sign of postpartum depression observed during a pregnancy period, since the information related to stress is output to both of the expectant woman and the consulting business operator, the expectant woman is made to know that there is a sign of postpartum depression and, at the same time, it is possible to make the consulting business operator take care of the expectant woman. As a result, prevention of postpartum depression can be further expected.

Further, in the present aspect, the information to be output to the first information terminal may include display information for allowing the user to select whether to accept contact of the consulting business operator with the user.

Some users do not want a care from the consulting business operator. In the present aspect, since the user can choose whether to accept the access from the consulting business operator, it is possible to flexibly deal with user's needs.

Further, in the above aspect, the information related to the stress of the user may be used to call the user's attention to a need for reducing stress build up in the user.

In this case, since the user is notified of the information indicating that the stress is in a state where the stress needs to be paid attention to, the user is made to know, in an early stage, that stress is accumulated, and it is thus possible to prevent the user from developing postpartum depression.

Further, in the above aspect, the information related to the stress of the user may indicate that the stress of the user is more than the predetermined normal range.

In this case, since the information indicating that the stress exceeds the predetermined normal range is notified to the user, it is possible to notify the user of the information objectively indicating that stress is accumulated, and it is thus possible to make the user effectively know that there is a sign of postpartum depression.

Further, in the above aspect, the sensor for detecting heptadecane may be built in a device to be worn on the user.

In this case, since the sensor to detect heptadecane is embedded in the device to be mounted on the user, it is possible to enable an object mounted on a user in a daily life to have a function of the sensor, for example. As a result, it is possible to reduce hassle of the user wearing the sensor.

Further, in the above aspect, the information processing system may be configured to acquire the biogas information along with a user ID of the user, and to output the information related to stress on the user to the information terminal associated with the user ID of the user.

In this case, since the biological gas information is acquired together with the user ID, the biological gas information can be managed for each user, and it is thus possible to prevent that a sign of postpartum depression of one user is determined by using biological gas information of some other users. Further, since the information related to stress is transmitted to the information terminal related to the user ID, it is possible to prevent the information related to stress from being transmitted to an information terminal not related to the user ID and to thus protect privacy of the user.

Further, an information processing system according to another aspect of the present disclosure includes a server device, and an information terminal. The server device is configured to:

acquire biological gas information presenting a concentration of heptadecane of a user acquired by a sensor that detects heptadecane discharged from a skin surface of the user, obtain reference information representing an upper limit of a normal range of the concentration of heptadecane per unit period of time, using a memory storing the reference information representing the upper limit of the normal range, and output information related to stress of the user to the information terminal after it is determined that a frequency that the concentration of heptadecane of the user per the unit period of time is more than the upper limit of the normal range tends to increase, based on the biological gas information acquired in a pregnancy period of the user.

The information terminal displays the information related to stress of the user on the display of the information terminal.

Further, an information terminal according to another aspect of the present disclosure is used in the above information processing system.

Further, an information processing method according to still another aspect of the present disclosure is an information processing method using a computer. The method comprising:

acquiring, via a network, biological gas information representing a concentration of heptadecane of a user acquired by a sensor that detects heptadecane discharged from a skin surface of the user;

obtaining reference information representing an upper limit of a normal range of the concentration of heptadecane per unit period of time, using a memory storing the reference information representing the upper limit of the normal range; and outputting information related to stress of the user to display on a display the information related to stress of the user after it is determined a frequency that the concentration of heptadecane of the user per the unit period of time is more than the upper limit of the normal range tends to increase, based on the biological gas information acquired in a pregnancy period of the user.

The present aspect is supposed to perform processing on, for example, a local computer.

First Embodiment (Prediction Data)

FIGS. 6A and 6B are graphs each showing prediction data of biological data dealt in a first embodiment of the present disclosure. In each of FIGS. 6A and 6B, the vertical axis represents biological gas concentration (an example of the biological gas information), and the horizontal axis represents time. The prediction data does not represent actually measured biological data but just data made by predicting biological data. The biological data is the biological data measured by a sensor mounted on the user as will be mentioned below. The biological data represents measurement values of a concentration of a measurement object biological gas (biological gas concentration) of the biological gases released from a skin surface of a user. In the present disclosure, the biological gas to be a measurement object is heptadecane. A unit of the biological gas concentration is μg/dL, for example.

FIG. 6A shows a temporal transition of the biological data of the user when no stress is applied, and FIG. 6B shows a temporal transition of the biological data of the user when stress is applied. As shown in FIG. 6A, regarding the biological data when no stress is applied, the biological gas concentration is within the normal range. On the other hand, as shown in FIG. 6B, regarding the biological data when stress is applied, a frequency with which the biological gas concentration exceeds an upper limit DH of the normal range is higher. In the example of FIG. 6B, the biological gas concentration exceeds the upper limit DH four times in a time slot from 06:00 to 24:00.

In view of the above, in the present disclosure, if it is detected that there is an increasing tendency in a frequency with which the biological gas concentration exceeds the upper limit DH, it is determined that the user shows a sign of postpartum depression, and it is prevented that the user develops postpartum depression, by making the user know that there is a sign of postpartum depression and prompting a consulting business operator to take care of the user.

(Sensor)

Figure 7:
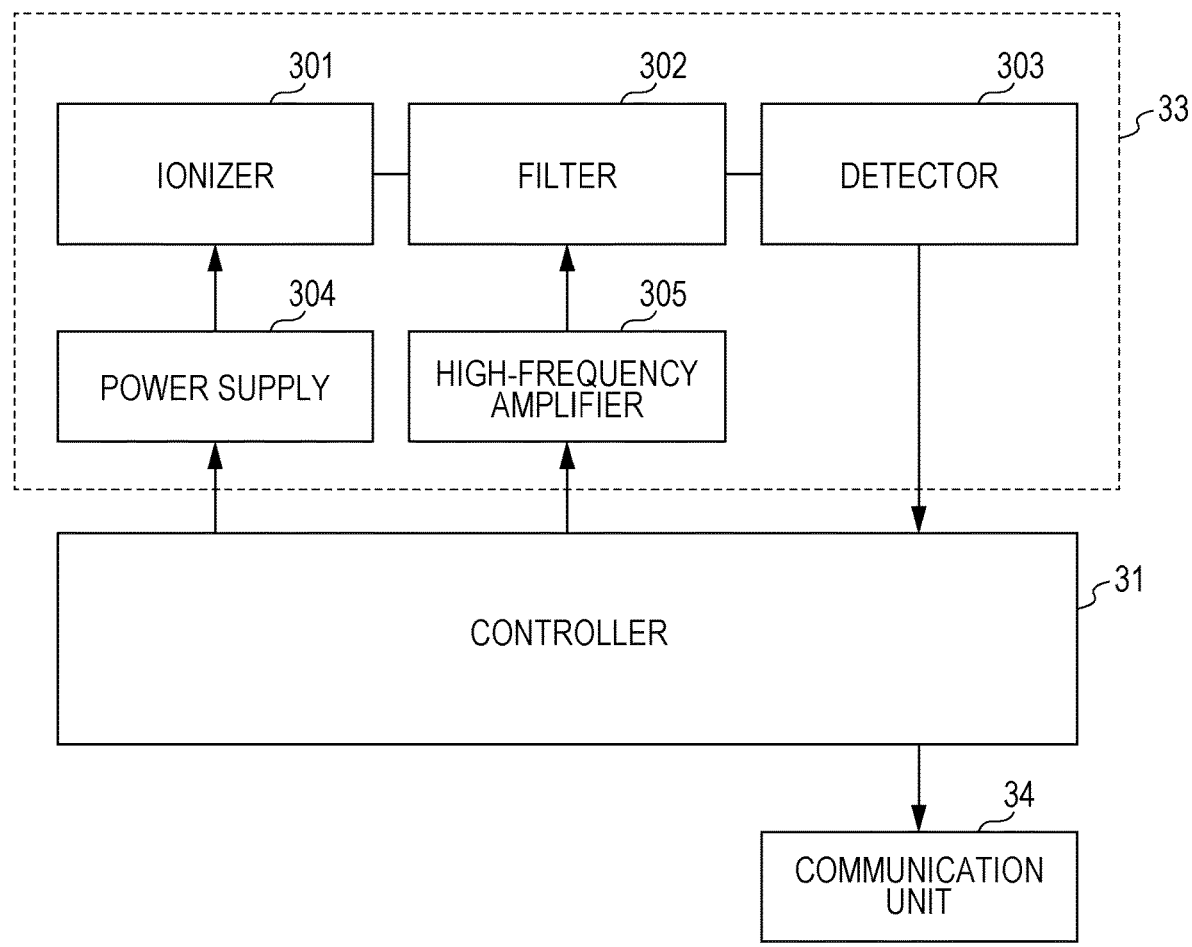
FIG. 7 is a block diagram showing an example of a configuration of a sensor for measuring biological data in the first embodiment of the present.

FIG. 7 is a block diagram showing an example of a configuration of sensor 3 that measures the biological data in the first embodiment of the present disclosure.

As sensor 3, in the present disclosure, there is used a sensor using, for example, the technology of Field Asymmetric Ion Mobility Spectrometry (FAIMS). The field asymmetric ion mobility spectrometer is used to selectively separate one type of substance from a mixture including two or more types of substances.

Sensor 3 includes detection unit 33, controller 31, and communication unit 34. Detection unit 33 includes ionizer 301, filter 302, detector 303, power supply 304, and high-frequency amplifier 305. Note that, in FIG. 7, the arrowed lines show flows of electric signals, and the lines connecting among ionizer 301, filter 302, and detector 303 show flow of the biological gas.

Power supply 304 and high-frequency amplifier 305 are respectively used to drive ionizer 301 and filter 302. From the biological gas ionized by using ionizer 301, only an intended biological gas (heptadecane in the present disclosure) is separated with filter 302, and an amount of ions having passed through filter 302 is detected by detector 303, so that information indicating the biological gas concentration is obtained. The obtained information is output via communication unit 34. Controller 31 controls driving of sensor 3.

Figure 8:
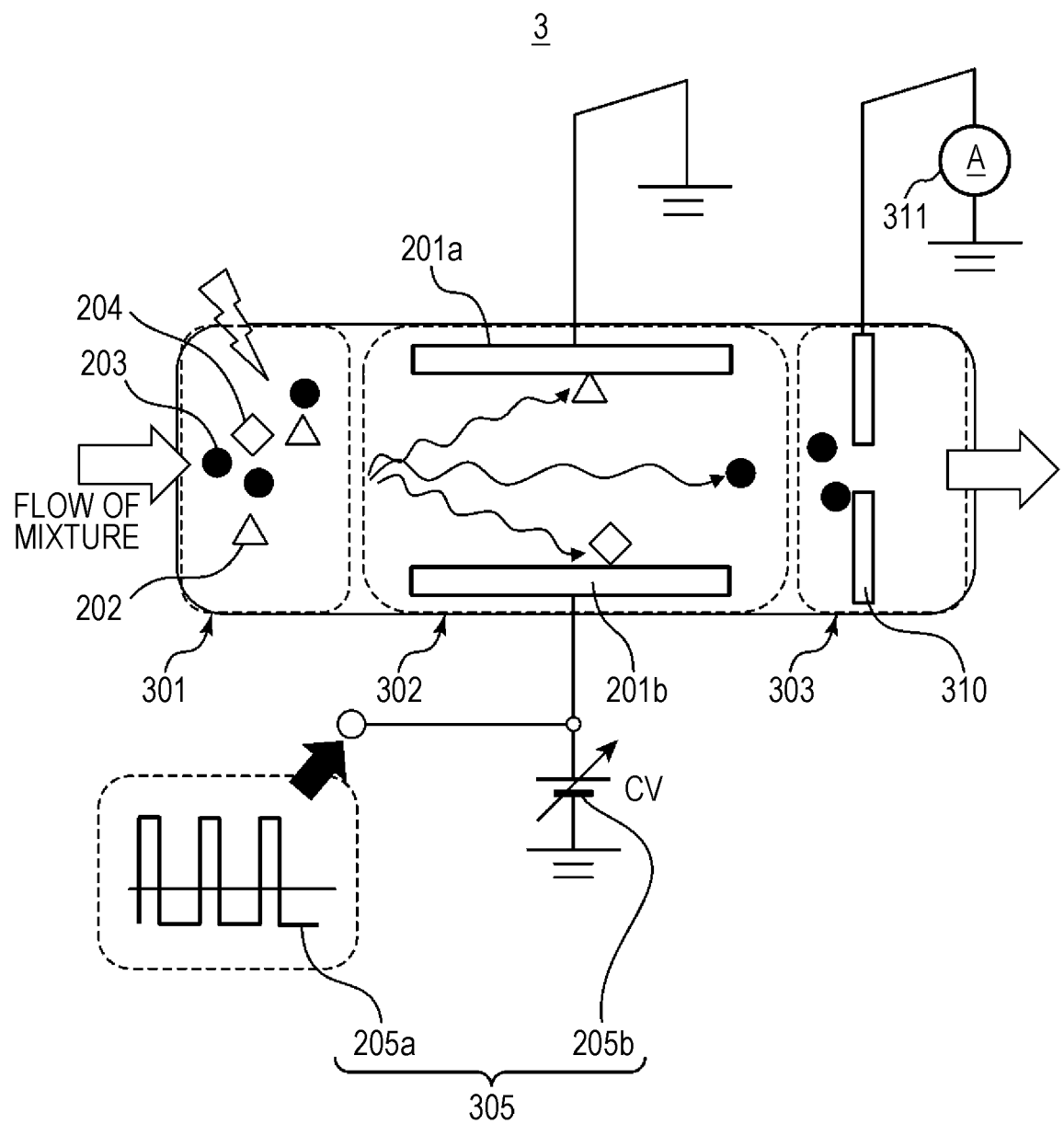
FIG. 8 is a diagram illustrating in more detail an operation of the sensor shown in FIG. 7.

FIG. 8 is a diagram illustrating in more detail an operation of sensor 3 shown in FIG. 7. A mixture supplied to ionizer 301 is the biological gas released from the skin surface of the user. Ionizer 301 may include an inlet for taking in the biological gas having been released from the skin surface of the user. Further, the inlet may be provided with an absorbent for absorbing the biological gas. In addition, a heater may be provided to desorb the biological gas absorbed in the absorbent from the absorbent. In the example of FIG. 8, the mixture is supposed to include three types of gases 202 to 204 for the purpose of description. Gases 202 to 204 are ionized by using ionizer 301.

Ionizer 301 includes a corona discharge source, a radiation source, and other units and ionizes gases 202 to 204. Ionized gases 202 to 204 are supplied to filter 302 disposed adjacent to ionizer 301. Note that the corona discharge source and the radiation source constituting ionizer 301 are driven by a voltage supplied from power supply 304.

Filter 302 includes first electrode 201a and second electrode 201b each provided parallel to each other and having a flat plate shape. First electrode 201a is grounded. On the other hand, second electrode 201b is connected to high-frequency amplifier 305.

High-frequency amplifier 305 includes AC voltage source 205a for generating an asymmetric AC voltage and variable voltage source 205b for generating a compensation voltage CV, which is a DC voltage. AC voltage source 205a generates the asymmetric AC voltage and applies the asymmetric AC voltage to second electrode 201b. One end of variable voltage source 205b is connected to second electrode 201b, and the other end is grounded. With this arrangement, the asymmetric AC voltage generated by AC voltage source 205a is superposed with the compensation voltage CV and is suppled to second electrode 201b.

Between first electrode 201a and second electrode 201b, three types of gases 202 to 204 having been ionized are supplied. Three types of gases 202 to 204 are influenced by the electric field generated between first electrode 201a and second electrode 201b.

Figure 9:
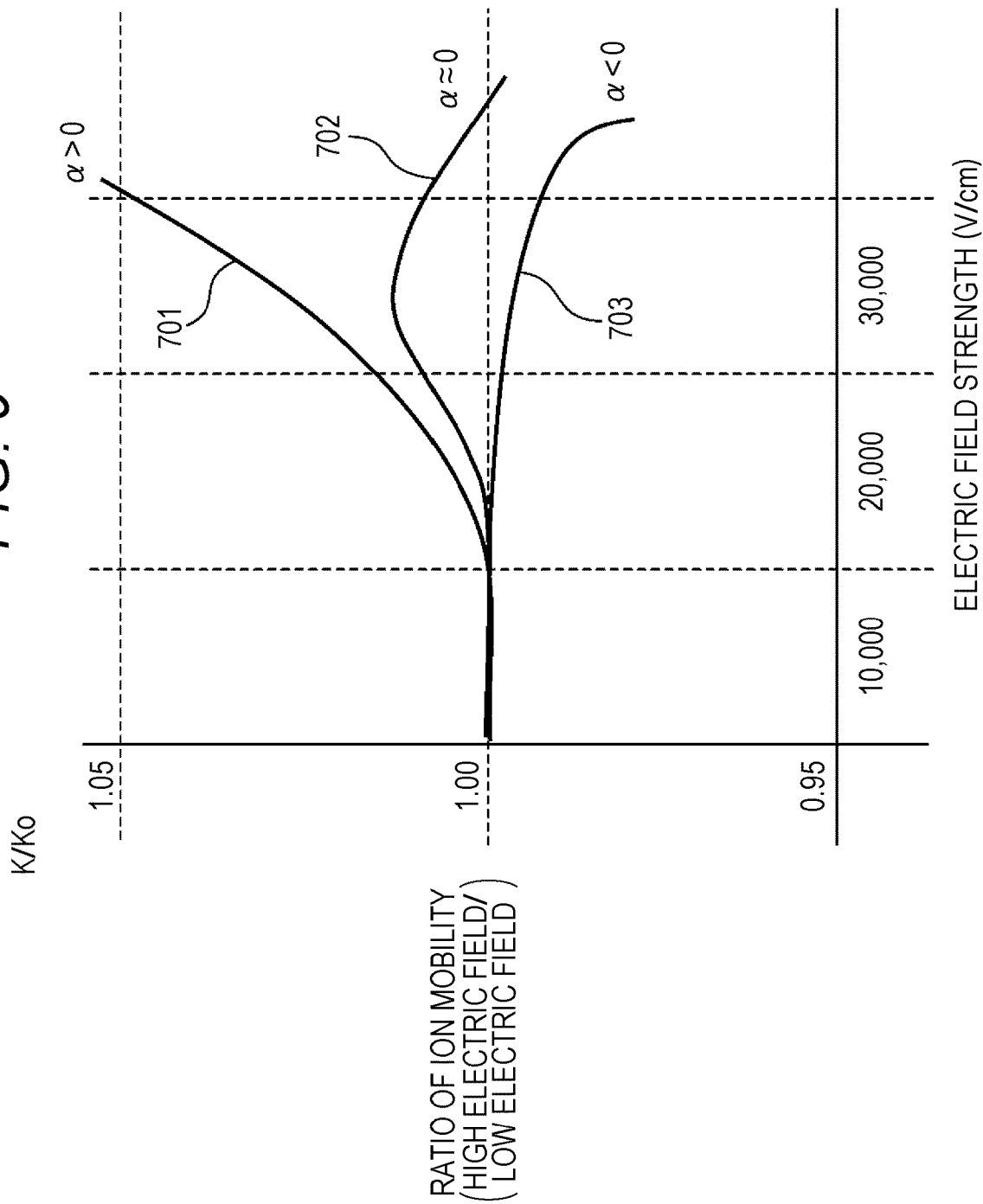
FIG. 9 is a graph showing a relationship between an electric field intensity and a ratio of ion mobility.
Figure 10:
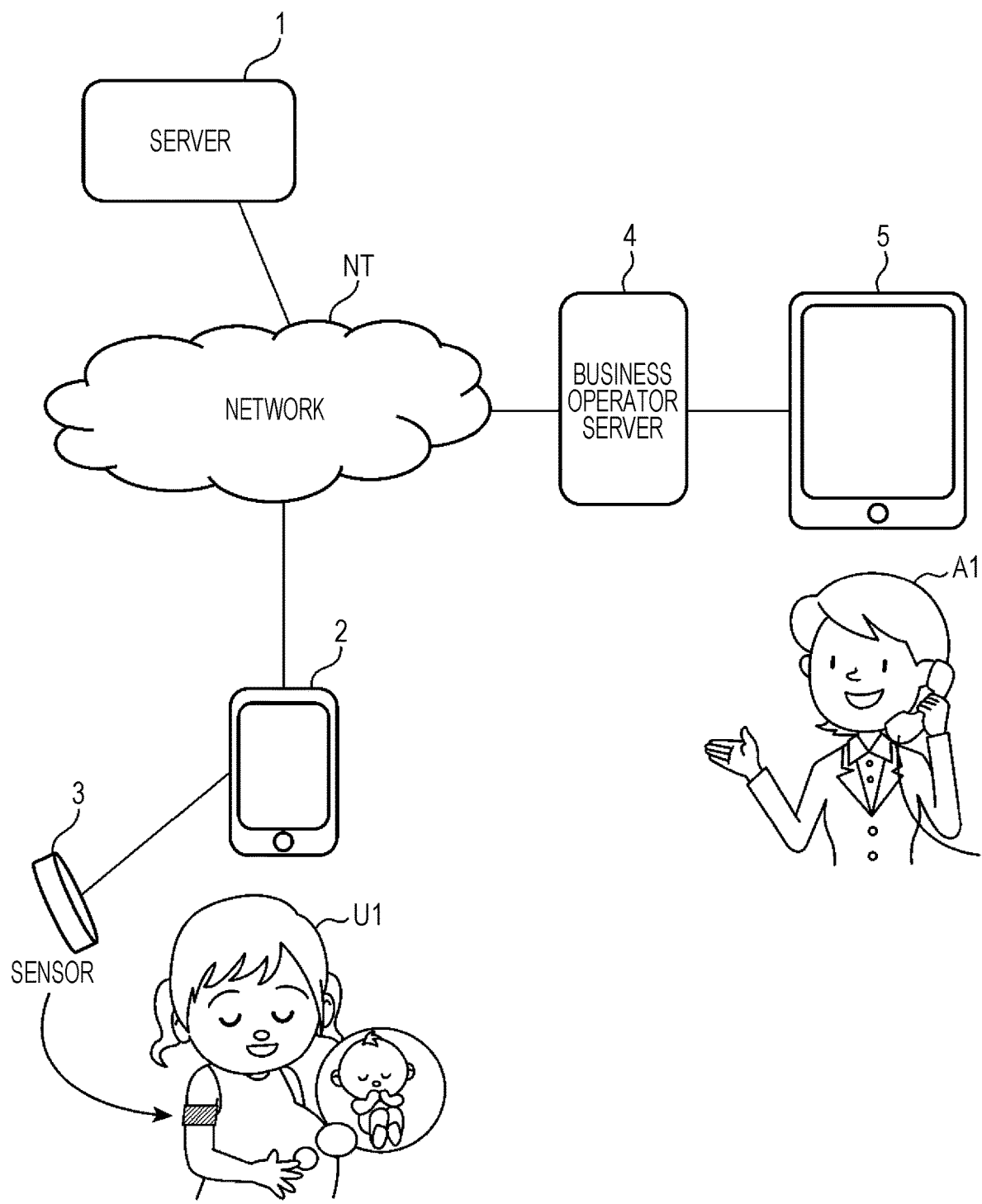
FIG. 10 is a diagram showing an example of a network configuration of an information processing system according to the first embodiment of the present disclosure.

FIG. 9 is a graph showing a relationship between an electric field intensity and a ratio of ion mobility, the vertical axis represents the ratio of ion mobility, and the horizontal axis represents the electric field intensity (V/cm). The coefficient α depends on the type of ion. The ratio of ion mobility represents the ratio of the mobility in high electric fields to the ion mobility in the small electric field limit.

As represented by curved line 701, the ionized gas with a coefficient α>0 moves more actively when the electric field intensity increases. The ion having a mass-to-charge ratio smaller than 300 moves in this way.

As represented by curved line 702, the ionized gas with the coefficient α, which is almost 0, moves more actively when the electric field intensity increases; however, the mobility of the ionized gas decreases when the electric field intensity further increases.

As represented by curved line 703, the mobility of the ionized gas with the coefficient α, which is negative, decreases when the electric field intensity increases. An ion having a mass-to-charge ratio of greater than or equal to 300 moves in this way.

Because of the differences between the mobilities, three types of gases 202 to 204 move in different directions inside filter 302 as shown in FIG. 8. In the example of FIG. 8, only gas 203 is discharged from filter 302. On the other hand, gas 202 is trapped by a surface of first electrode 201a, and gas 204 is trapped by a surface of second electrode 201b. In this way, from three types of gases 202 to 204, only gas 203 is selectively separated and is discharged from filter 302. That is, on sensor 3, when the electric field intensity is appropriately set, an intended gas can be discharged from filter 302. Note that the electric field intensity is determined by the voltage value of the compensation voltage CV and a waveform of the asymmetric AC voltage generated by AC voltage source 205a. Therefore, sensor 3 can discharge the biological gas to be the measurement object from filter 302 by setting the voltage value of the compensation voltage CV and the waveform of the asymmetric AC voltage to a predetermined voltage value and waveform, depending on the type (heptadecane in the present disclosure) of the biological gas to be the measurement object.

Detector 303 is disposed adjacent to filter 302. In other words, filter 302 is disposed between ionizer 301 and detector 303. Detector 303 includes electrode 310 and ammeter 311 to detect gas 203 having passed through filter 302.

Gas 203 having reached detector 303 delivers an electric charge to electrode 310. The value of a current flowing in proportion to the amount of the delivered electric charge is measured by ammeter 311. From the value of the current measured by ammeter 311, the concentration of gas 203 is measured.

(Network Configuration)

FIG. 10 is a diagram showing an example of a network configuration of the information processing system according to the first embodiment of the present disclosure. The information processing system provides a care service for taking care of stress of user U1. This care service is provided by, for example, an insurance company or the like with which user U1 is contracted. Note that the care service may be actually performed by, for example, a manufacturer that manufactures sensor 3 and that is subcontracted by the insurance company. Alternatively, the care service may be provided by a service provider different from the insurance company that provides the care service itself.

The insurance company provides user U1 with an insurance service such as life insurance and medical insurance. In this case, the insurance company prevents postpartum depression of user U1 by, for example, lending sensor 3 to user U1, acquiring biological data of user U1, and managing a stress state of user U1. This enables the insurance company to save spending of insurance money. Since this care service forces user U1 to wear sensor 3, some users U1 feel a burden. To address this issue, the insurance company may provide an insurance plan in which an insurance fee to be paid by user U1 is discounted in exchange for this care service.

The information processing system includes: server 1 (an example of the server device); user terminal 2 (an example of the first information terminal); sensor 3; business operator server 4, and business operator terminal 5 (an example of the second information terminal).

Server 1, user terminal 2, and business operator server 4 are communicably connected to each other via network NT. Network NT is configured with a network including an internet communication network, a portable telephone communication network, and a public telephone line network. Sensor 3 and user terminal 2 are communicably connected to each other via short-range wireless communication such as wireless local area network (LAN) of IEEE802.11b, Bluetooth (registered trade mark, IEEE802.15.1), or the like. Further, business operator server 4 and business operator terminal 5 are communicably connected to each other via, for example, wired LAN (for example, IEEE802.3), wireless LAN (for example, IEEE802.11b), or the like.

Server 1 is configured with, for example, a cloud server including one or more computers. Server 1 includes: a processor such as a central processing unit (CPU), a field programmable gate array (FPGA), or the like; and a memory. Server 1 acquires the biological data of user U1 measured by sensor 3 via user terminal 2 and network NT, and determines whether the biological gas concentration is within the normal range.

User terminal 2 is configured with a portable information processing device such as a smartphone, a tablet terminal, or the like. However, user terminal 2 may be configured with a stationary computer. User terminal 2 is held by user U1. In the present disclosure, user U1 is, for example, an expectant woman who receives a care service.

Business operator server 4 is configured with, for example, a cloud server including one or more computers. Business operator server 4 includes: a processor such as a CPU, an FPGA, or the like; and a memory. Business operator server 4 connects business operator terminal 5 to network NT and manages business operator terminal 5.

Business operator server 4 is managed by, for example, a consulting business operator to which representative A1, who takes care of user U1 through business operator terminal 5, belongs. The consulting business operator may be, for example, a company that is subcontracted by the insurance company or may be the insurance company. Representative A1 receives a talk about an insurance service and a care service, from user U1 through telephone or the like. In particular, in the present disclosure, when user U1 shows a sign of postpartum depression, representative A1 makes communication with user U1 and takes care of user U1 under permission of user U1.

Sensor 3 is mounted on, for example, an arm of user U1 and detects the concentration of the biological gas released from an underarm of user U1. Sensor 3 includes, for example, a fitting belt, and a user winds the fitting belt around the arm at a position close to the underarm, so that sensor 3 is attached in the vicinity of the underarm. This arrangement enables sensor 3 to detect the biological gas released from the underarm. As the position, on the arm, in the vicinity of the underarm, it is possible to employ, for example, a position that is on the arm and is slightly close to the elbow from a connection point between the body and the arm. Note that when it is considered that the biological gas is released much from the underarm, sensor 3 is preferably attached, for example, in such a manner that the inlet for collecting the biological gas is located on the rear side of the arm. In this case, the reason why sensor 3 is attached at the position, on the arm, in the vicinity of the underarm is that it is difficult to attach sensor 3 to the underarm itself. However, this is an example. For example, sensor 3 may be attached to an underarm part of a shirt to be put on user U1. This arrangement enables sensor 3 to face the underarm, and the biological gas can be more surely collected. Note that this shirt is an example of the device to be mounted on a user.

Business operator terminal 5 is configured with, for example, a stationary computer owned by the consulting business operator and is used by representative A1. Note that business operator terminal 5 may be configured with a portable information processing device such as a smartphone, a tablet terminal, or the like.

FIG. 11 is a block diagram showing an example of a detailed configuration of the information processing system shown in FIG. 10. Server 1 includes controller 11, memory 12, and communication unit 13. Controller 11 is configured with a processor and includes data analyzer 111. Data analyzer 111 is realized by, for example, a processor executing a program making a computer execute an information provision method, of the present disclosure, stored in memory 12. Note that the program making a computer execute an information provision method of the present disclosure may be provided by download through a network or may be provided by way of a computer-readable non-volatile recording medium storing the program.

If communication unit 13 receives the biological data obtained by sensor 3, data analyzer 111 acquires the biological data from communication unit 13. Then, data analyzer 111 reads out from memory 12 the information indicating the upper limit DH of the normal range of the biological gas concentration, and determines whether the biological gas concentration indicated by the biological data exceeds the upper limit DH. Then, data analyzer 111 registers the biological data in biological data table T4 (FIG. 12) stored in memory 12, in association with a result of the determination. Further, when the biological data has been accumulated for a prescribed period (for example, one day, half a day, or two days), data analyzer 111 counts cases where the biological gas concentration exceeded the upper limit DH in the biological data in the prescribed period. Then data analyzer 111 determines whether there is an increasing tendency in the frequency with which the biological gas concentration exceeds the upper limit DH, by comparing a count number of cases where the biological gas concentration exceeded the upper limit DH in one or a consecutive plurality of past prescribed periods with the count number in this prescribed period. Then, if data analyzer 111 determines that there is an increasing tendency, data analyzer 111 transmits information related to stress to user terminal 2 and business operator terminal 5 via communication unit 13.

Figure 12:
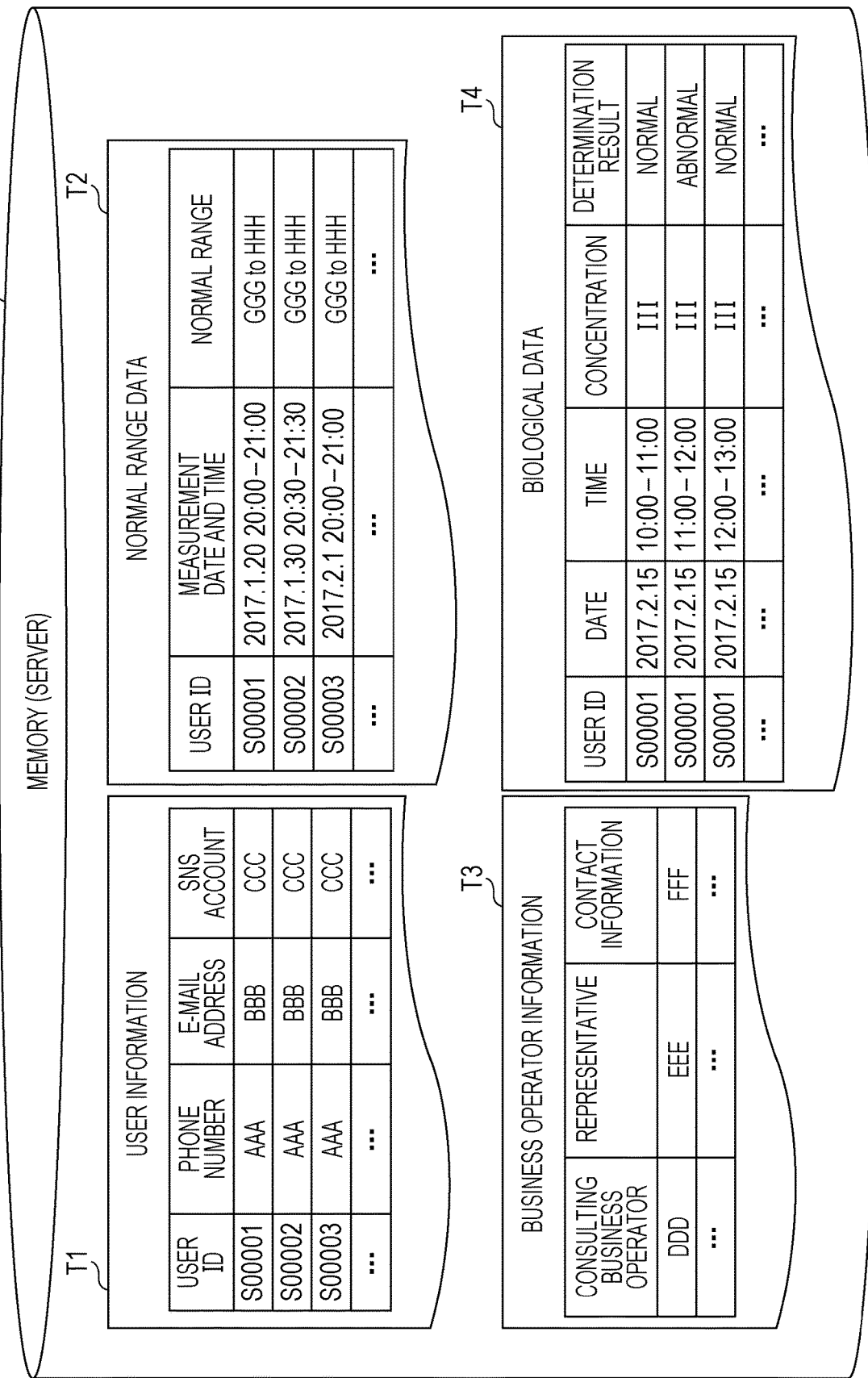
FIG. 12 is a diagram showing an example of data configurations of tables stored in a memory.

Memory 12 stores information indicating the normal range of the biological gas concentration. In the present disclosure, as shown in FIG. 12, memory 12 stores user information table T1, normal range data table T2, business operator information table T3, and biological data table T4. FIG. 12 is a diagram showing an example of data configurations of the tables stored in memory 12.

User information table T1 stores personal information of one or more users who receive a care service. In user information table T1, one record is assigned to one user, and "user ID", "telephone number", "e-mail address", and "social networking service (SNS) account" are stored in association with each other. Note that "telephone number", "e-mail address", "SNS account" are an example of the destination information.

In a "user ID" field, there is stored an identifier for uniquely identifying a user who receives a care service. In a "telephone number" field, there are stored telephone numbers of a user's home and user terminal 2. In an "e-mail address" field, there is stored an e-mail address of user terminal 2 of each user. In an "SNS account" field, there is stored account information for logging in an SNS site that each user set up.

Normal range data table T2 stores the normal ranges of stress of the biological gas concentrations of one or more users who receive a care service. In normal range data table T2, one record is assigned to one user, and "user ID", "measurement date and time", and "normal range" are stored in association with each other.

In a "user ID" field, there is stored a user ID that is the same as the user ID in user information table T1. In a "measurement date and time" field, there is stored a time slot corresponding to a measurement date and time of the biological data used to calculate the normal range. In a "normal range" field, there is stored the normal range calculated by using the biological data stored in the "measurement date and time" field. In the "normal range" field, there are stored a lower limit DL and an upper limit DH of the normal range.

For example, regarding a user with the user ID "S00001", the normal range is calculated by using the biological data measured in the time slot from 20:00 to 21:00 on Jan. 20, 2017.

As described above, in the present disclosure, since the normal range is already calculated for each user, stress can be determined for each user by using the normal range appropriate to each user, so that determination accuracy can be improved. In the present disclosure, the normal range is calculated for each user, but this is just an example, and it is possible to use an average value of the normal ranges calculated for a part of all the users, as the normal range for all the users. Alternatively, an average value of the normal ranges of all the users may be used as the normal range for all the users. In these cases, it is not necessary to store or calculate the normal range for each user, and it is thus possible to save memory consumption and to reduce process steps.

Business operator information table T3 stores information of one or more consulting business operators. In business operator information table T3, one record is assigned to one consulting business operator. Business operator information table T3 stores "consulting business operator", "representative", and "contact information" in association with each other. In a "consulting business operator" field, there is stored a name of the consulting business operator. In a "representative" field, there is stored a name of a representative belonging to the consulting business operator. In a "contact information" field, there is stored contact information of a representative. As the contact information of a representative, it is possible to employ the e-mail address and the telephone number of business operator terminal 5 of the representative. Note that the "contact information" is an example of the destination information.

Biological data table T4 stores the biological data obtained by sensor 3. In biological data table T4, one record is assigned to one piece of biological data, and "user ID", "date", "time", "concentration", and "determination result" are stored in association with each other.

In a "user ID" field, there is stored a user ID that is the same as the user ID stored in user information table T1. In a "date" field, there is stored a measurement date of the biological data. In a "time" field, there is stored the time slot when the biological data was measured. In a "concentration" field, there is stored the biological gas concentration indicated by the biological data. In a "determination result" field, there is stored the determination result whether the biological gas concentration is within the normal range. Note that in the "time" field, there may be stored the time slot when the biological data was acquired by server 1.

For example, in the record on the first row of biological data table T4, there is stored the biological data, which is the biological gas concentration "OO", of the user with the user ID "S00001" measured in the time slot 10:00 to 11:00 on Feb. 15, 2017. In addition, in the record on the first row, there is "Normal" stored in the "Determination result" field because the biological gas concentration is within the normal range. On the other hand, in the record on the second row, there is stored "Abnormal" in the "Determination result" field because the biological gas concentration was out of the normal range.

Note that biological data table T4 shows only the biological data of the user with the user ID "S00001". However, this is just an example, and in biological data table T4 there is stored the biological data of all of the users who receive a care service.

Refer back to FIG. 11 again. Communication unit 13 is configured with, for example, a communication circuit that connects server 1 to network NT, and communication unit 13 receives the biological data measured by sensor 3 and transmits the information related to stress to user terminal 2 and business operator terminal 5.

User terminal 2 includes controller 21, memory 22, display unit 23 (an example of the display), and communication unit 24. Controller 21 is configured with a processor such as a CPU, and performs overall control of user terminal 2. Memory 22 stores various types of data. In the present disclosure, memory 22 stores, in particular, an application to be performed on user terminal 2 to make user U1 receive a care service. In addition, memory 22 stores the user ID in association with biological data.

Display unit 23 is configured with, for example, a display including a touch panel, and displays various types of information. In the present disclosure, display unit 23 displays, in particular, the information related to stress. Communication unit 24 is configured with a communication circuit that connects user terminal 2 to network NT and, at the same time, makes user terminal 2 communicate with sensor 3. In the present disclosure, communication unit 24 receives, in particular, the biological data transmitted from sensor 3 and transmits the received biological data to server 1 in association with the user ID stored in memory 22. Further, in the present disclosure, communication unit 24 receives, in particular, the information related to stress transmitted from server 1. Note that display unit 23 does not have to be configured with a touch panel. In this case, user terminal 2 only has to include an operation unit to receive an operation from the user.

Sensor 3 includes controller 31, memory 32, detection unit 33, and communication unit 34. Controller 31 is configured with a processor such as a CPU or a digital signal processor (DSP), and performs overall control of sensor 3. Memory 32 temporarily stores, for example, the biological data measured by detection unit 33. In addition, memory 32 stores data (for example, a frequency and amplitude on the positive side and amplitude on the negative side) that is necessary for AC voltage source 205a to generate the asymmetric AC voltage. Further, memory 32 stores a voltage value of the compensation voltage CV.

Communication unit 34 is configured with a communication circuit for wireless LAN, Bluetooth (registered trademark), or the like, and transmits the biological data measured by detection unit 33 to user terminal 2. This biological data is received by communication unit 24 of user terminal 2 and is transmitted to server 1 via network NT.

Business operator server 4 includes controller 41, memory 42, and communication unit 43. Controller 41 is configured with a processor such as a CPU or an FPGA, and performs overall control of business operator server 4. Memory 42 stores a computer-readable program to make a computer function as business operator server 4.

Communication unit 43 is configured with a communication circuit that connects business operator server 4 to network NT and, at the same time, makes business operator server 4 communicate with business operator terminal 5. In the present disclosure, communication unit 43 receives, in particular, the information related to stress and transmits the received information to business operator terminal 5.

Business operator terminal 5 includes controller 51, memory 52, display unit 53, and communication unit 54. Controller 51 is configured with a processor such as a CPU, and performs overall control of business operator terminal 5. Memory 52 stores a computer-readable program to make the computer function as business operator terminal 5. Display unit 53 displays various images under control of controller 51. In the present disclosure, display unit 53 displays, in particular, the information related to stress transmitted from server 1. Communication unit 54 is configured with, for example, a communication circuit for wireless LAN or wired LAN. In the present disclosure, communication unit 54 receives, in particular, the information related to stress.

(Sequence)

Figure 11:
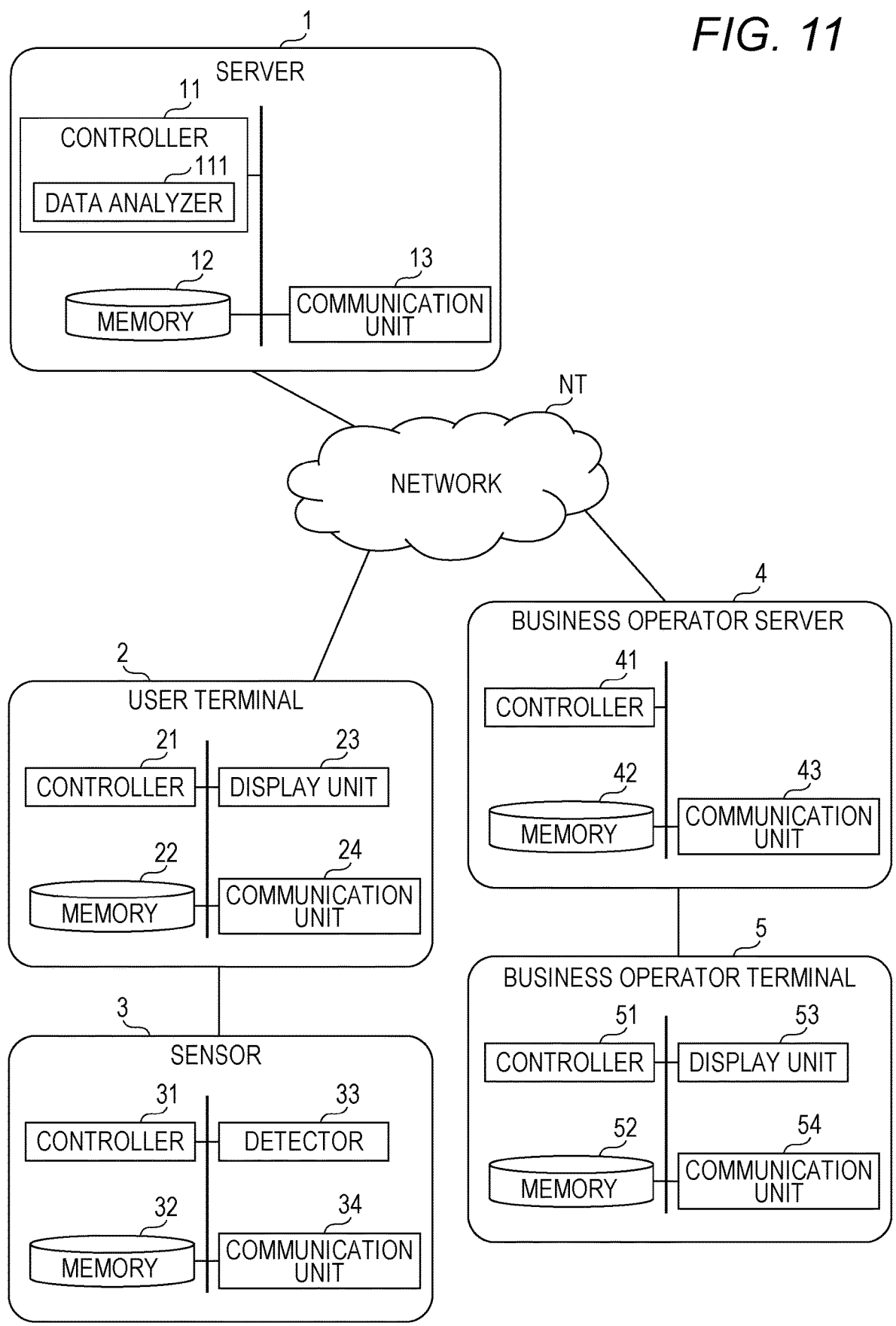
FIG. 11 is a block diagram showing an example of a detailed configuration of the information processing system shown in FIG. 10.
Figure 13:
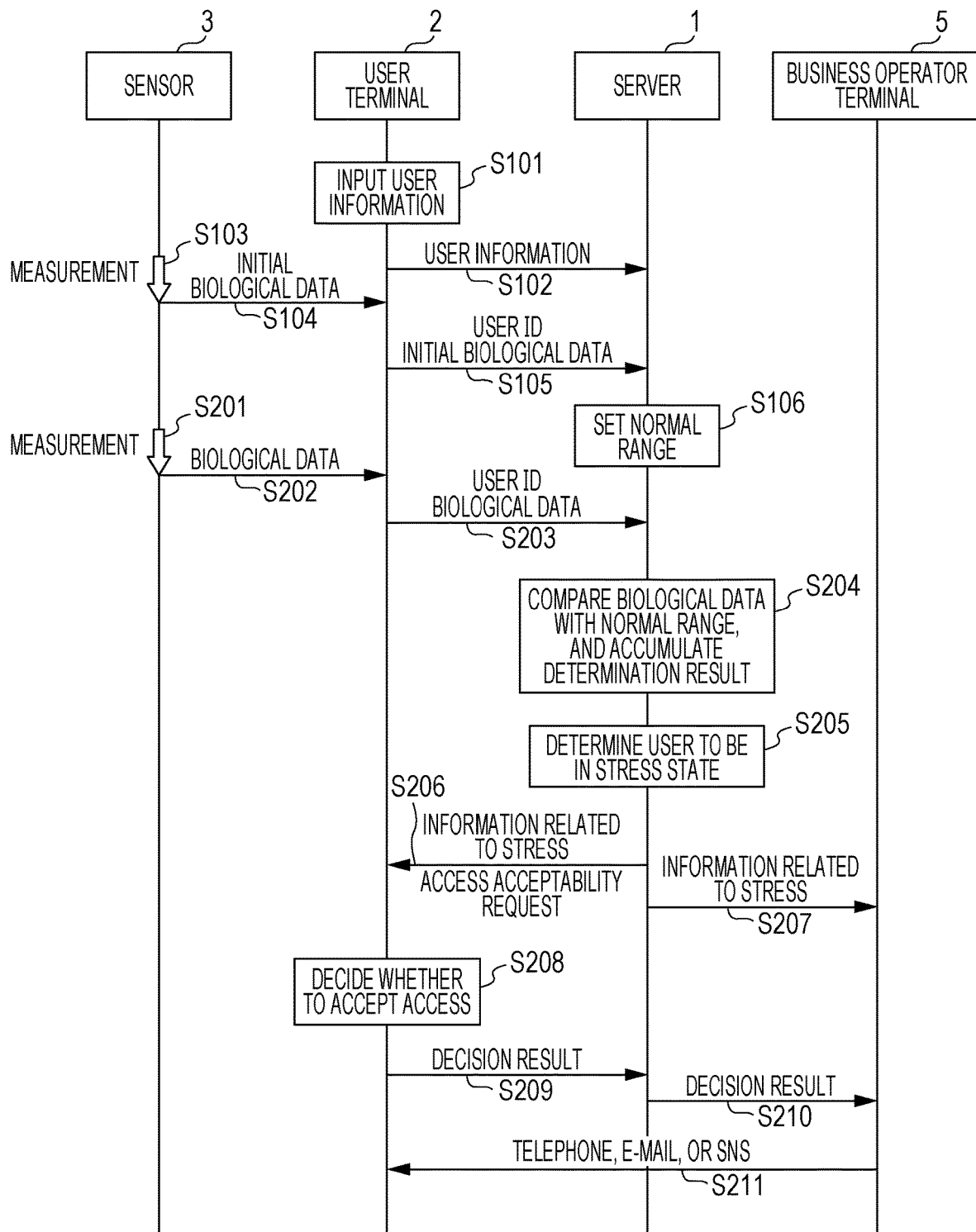
FIG. 13 is a sequence diagram showing an example of a process in a biological information system shown in FIG. 11.

FIG. 13 is a sequence diagram showing an example of a process in the biological information system shown in FIG. 11. This sequence diagram is divided into an initial phase from step S101 to step S106 and a normal phase including step S201 and steps subsequent thereto. The initial phase is for calculating the normal range of a user and is performed immediately after the care service is introduced. The normal phase is for monitoring the stress state of a user by using the normal range calculated in the initial phase.

The initial phase is performed, for example, when the application for user terminal 2 for receiving the care service is started on user terminal 2 by a user for the first time.

First, display unit 23 of user terminal 2 receives input of user information (step S101). In this step, display unit 23 may allow the user to input user information by displaying a registration screen to allow the user to input the user information such as a user ID, a telephone number, an e-mail address, an SNS account, and the like. Here, as the user ID, it is possible to use the user ID issued when the user makes an insurance contract with an insurance company, for example. Alternatively, the user ID may be the user ID issued by server 1 and notified to user terminal 2 when server 1 receives the user information in step S102 to be described later. In this case, the user does not have to input a user ID on the registration screen.

Next, controller 21 of user terminal 2 transmits the user information having been input to server 1 by using communication unit 24 (step S102). The transmitted user information is stored in user information table T1 by controller 41 of server 1.

Next, detection unit 33 of sensor 3 measures the initial biological data of the user (step S103). Next, controller 31 of sensor 3 transmits the measured initial biological data to user terminal 2 by using communication unit 34 (step S104).

On user terminal 2, if communication unit 24 receives the initial biological data, controller 21 transmits the initial biological data to server 1 in association with the user ID (step S105).

Because the initial biological data is used to calculate the normal range of the user, it is a precondition that the user is not in a stress state. For this reason, after the transmission of the user information is finished (step S102), user terminal 2 may cause display unit 23 to display, for example, a message such as "Biological data will be measured. Please wear the sensor and stay calm for a while". Data analyzer 111 of server 1 sets the normal range (step S106). The normal range having been set is stored in normal range data table T2 in association with the user ID by data analyzer 111 of server 1.

This completes the initial phase. Subsequently, the normal phase will be performed.

First, on sensor 3, detection unit 33 measures biological data (step S201), and controller 31 transmits the biological data to user terminal 2 by using communication unit 34 (step S202).

Next, on user terminal 2, when communication unit 24 receives the biological data, controller 21 transmits the biological data to server 1 by using communication unit 24 in association with the user ID (step S203).

Next, on server 1, when communication unit 13 receives the biological data, data analyzer 111 compares the biological data to the normal range and accumulates the determination result (step S204). In this step, the determination result is accumulated in the "determination result" field in the record for the concerning user in normal range data table T2, by using the user ID as a key.

Next, if data analyzer 111 determines that the user is in a stress state (step S205), data analyzer 111 transmits the information related to stress together with an access acceptability request to user terminal 2 (step S206). In addition, data analyzer 111 transmits the information related to stress also to business operator terminal 5 by using communication unit 13 (step S207).

Next, on user terminal 2, when communication unit 24 receives the information related to stress, controller 21 inquires the user, by using display unit 23, whether the user accepts access, and receives a decision result from the user (step S208). In this step, controller 21 may display, on display unit 23, an image including a "YES" button to permit contact from the consulting business operator and a "NO" button not to permit the contact. Then, if the "YES" button is chosen by the user, controller 21 determines that the user permits access from the consulting business operator, and may transmit the decision result meaning permission of access. On the other hand, the "NO" button is chosen by the user, controller 21 determines that the user does not permit access from the consulting business operator, and may transmit the decision result meaning prohibition of access.

Next, on user terminal 2, communication unit 24 transmits the decision result to server 1 (step S209). Next, on server 1, communication unit 13 receives the decision result and transmits the received decision result to business operator terminal 5 (step S210).

Next, on business operator terminal 5, when communication unit 54 receives the decision result and if the decision result means permission of access, controller 51 contacts user terminal 2 of the concerning user by telephone, e-mail, or SNS (step S211). If the contact is made by telephone, the representative of the consulting business operator may directly make a phone call to tell a message showing concern for the user, for example. If the contact is made by e-mail, the representative of the consulting business operator may use business operator terminal 5 to compose an e-mail containing a message showing concern for the user and send the e-mail to the e-mail address of the concerning user, for example. If the contact is made by SNS, the representative of the consulting business operator may use business operator terminal 5 to log in an SNS site of the concerning user and send a message showing concern for the user, for example.

In this step, as a message showing concern for the user, a message such as "How has your physical condition been recently?" or "Is there anything annoying you?" can be used. When the user receives this message, the user replies to the representative's message. Such communications will be made between the representative and the user until the user is satisfied to some extent. In this way, the user can get a relief that the representative listened to the user's uneasiness and problem through the communications with the representative, and the stress state of the user is thus reduced.

Note that if it is not determined, in step S205, that the user is in a stress state, the processing in steps S206, S207, S208, S209, S210, and S211 is not performed. Server 1 and business operator terminal 5 communicate with each other via business operator server 4, but business operator server 4 is not shown in FIG. 13. However, this is just an example, and server 1 and business operator terminal 5 may directly communicate with each other not via business operator server 4.

Figure 14:
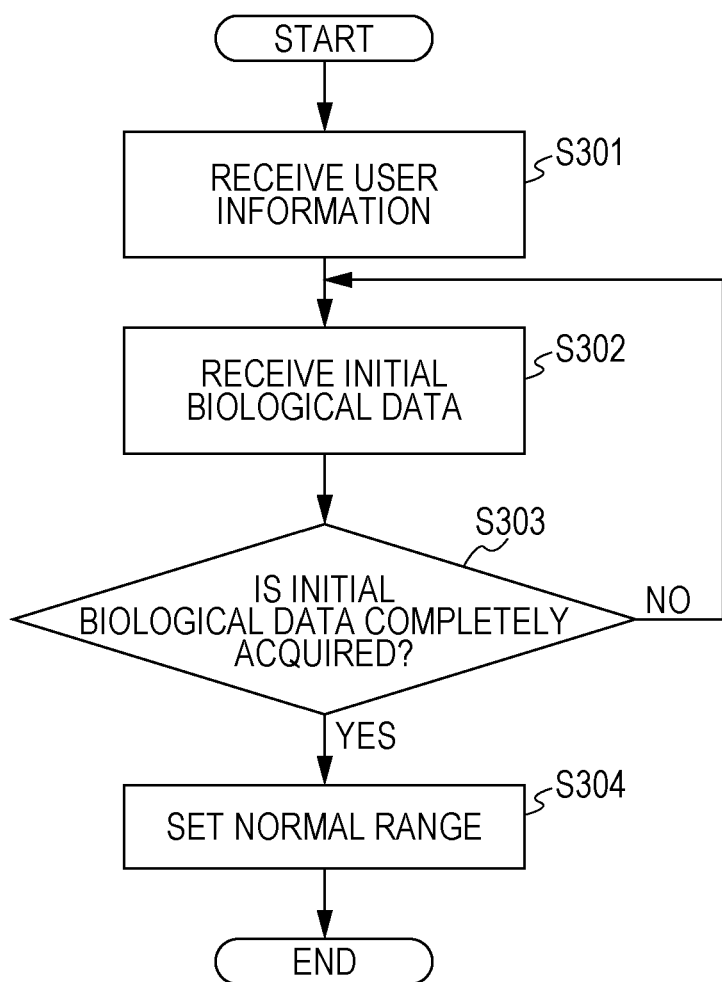
FIG. 14 is a flowchart showing details of an initial phase process according to the first embodiment of the present disclosure.

FIG. 14 is a flowchart showing details of the initial phase process according to the first embodiment of the present disclosure. The flowchart is executed on server 1. First, communication unit 13 receives the user information transmitted from user terminal 2 (step S301).

Next, communication unit 13 receives the initial biological data transmitted from user terminal 2 (step S302). Next, if the initial biological data is not completely acquired (step S303: NO), data analyzer 111 returns the process back to step S302. On the other hand, if the initial biological data is completely acquired (step S303: YES), data analyzer 111 proceeds the process to step S304. In this process, data analyzer 111 may finish acquisition of the initial biological data if the number of pieces of received initial biological data reaches a predetermined number sufficient to calculate the normal range or if a predetermined measurement period has elapsed since start of measurement of the initial biological data. In the present disclosure, as the measurement period for the initial phase, one hour, two hours, three hours, one day, two days, three days, or the like is used, for example, although depending on the measurement interval for the biological data. For example, if the measurement interval for the biological data is short, many pieces of initial biological data can be obtained in a short time, and the measurement period for the initial biological data can be accordingly reduced. For example, if one hour is used as the measurement interval for the biological data, half a day, one day, two days, three days, or the like is used as the measurement period for the initial biological data, for example. If one minute or one second is used as the measurement interval for the biological data, ten minutes, 20 minutes, one hour, two hours, three hours, or the like is used as the measurement period for the initial biological data, for example. However, these numerical values are just examples and can be changed appropriately.

Note that, in the present disclosure, since the user information was registered in the early stage of pregnancy, the measurement period for the initial biological data corresponds to an example of the predetermined period of an early stage of pregnancy of the user. The measurement interval for the biological data corresponds to an example of the unit period.

Next, data analyzer 111 sets the normal range by using the obtained initial biological data (step S304). Suppose, for example, the initial biological data as shown in FIG. 6A is obtained. In this case, data analyzer 111 extracts an upper limit peak and a lower limit peak of the biological gas concentration by analyzing the obtained initial biological data. Then, data analyzer 111 may calculate a value as the upper limit DH by adding a predetermined margin to the upper limit peak, and may calculate a value as the lower limit DL by subtracting a predetermined margin from the lower limit peak. Alternatively, data analyzer 111 may calculate a value as the upper limit DH by adding a predetermined margin to an average value of the upper-side peaks, and may calculate a value as the lower limit DL by subtracting a predetermined margin from an average value of the low-side peaks. By the above process, the normal range is set for each user.

Figure 15:
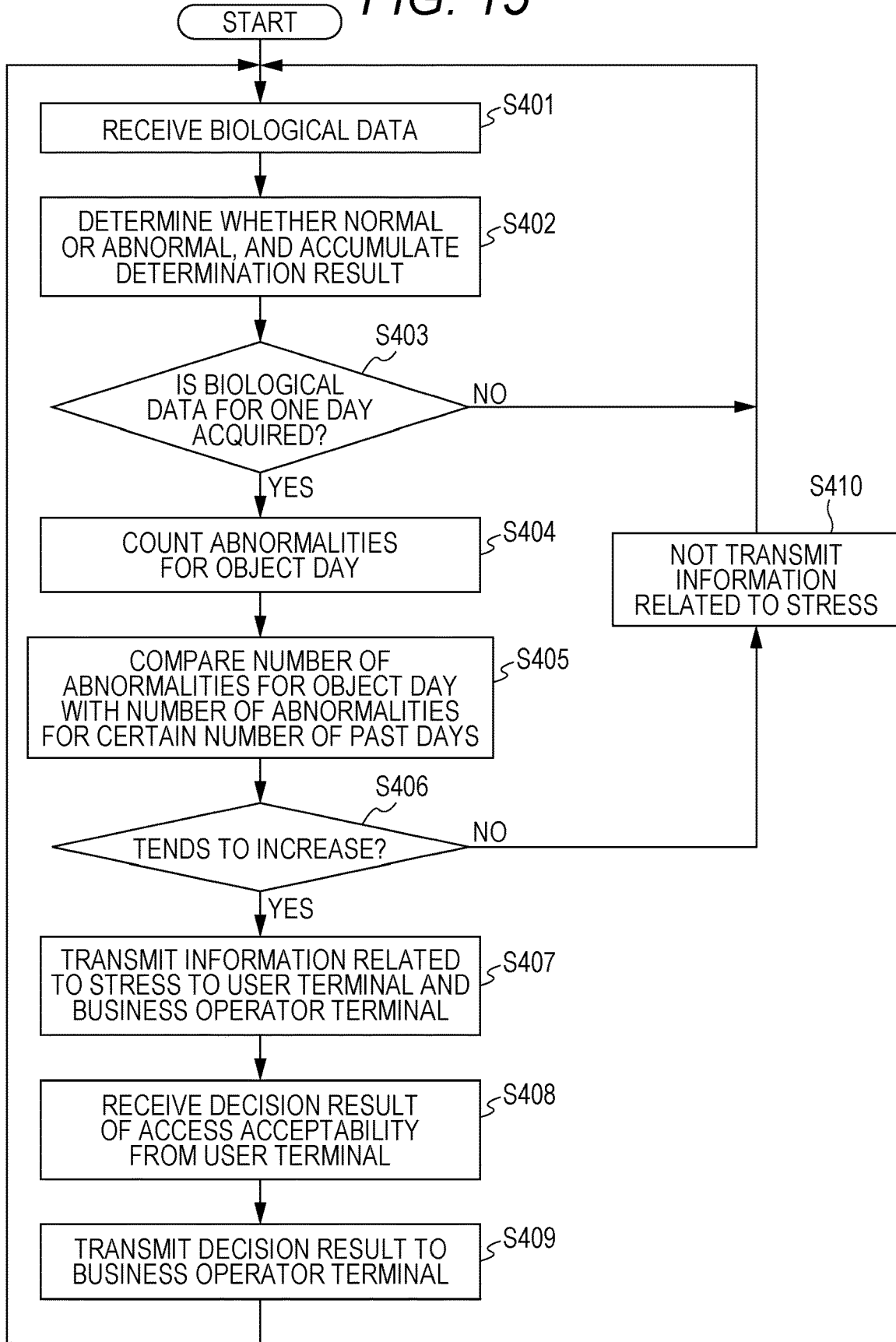
FIG. 15 is a flowchart showing details of a process of a normal phase according to the first embodiment of the present disclosure.

FIG. 15 is a flowchart showing details of the process of the normal phase according to the first embodiment of the present disclosure. Note that, the flowchart of FIG. 15 is periodically executed on server 1 at the measurement intervals of sensor 3 measuring the biological data. The following description shows, as an example, a case where one day is used as the prescribed period.

First, communication unit 13 receives the biological data from user terminal 2 (step S401). Next, data analyzer 111 determines whether the stress state is normal or abnormal, by comparing the biological gas concentration indicated by the biological data to the normal range for the concerning user, and data analyzer 111 accumulates the determination result in biological data table T4 (step S402). In detail, data analyzer 111 may store, in biological data table T4, the determination result in association with the user ID, the measurement date and time, and the biological gas concentration. Now refer to biological data table T4 of FIG. 12. On the record on the first row, there are written "2017.2.15" on the "date" field and "10:00-11:00" on the "time" field. This is because the measurement interval for the biological data is set to one hour and this biological data was measured between 10:00 and 11:00 on Feb. 15, 2017.

In the present disclosure, as the biological gas of the measurement object, heptadecane is used. Heptadecane has a positive correlation with intensity of stress. Therefore, data analyzer 111 may determine, if the biological gas concentration is greater than the upper limit DH of the normal range, that the stress state is abnormal and, if the biological gas concentration is lower than or equal to the upper limit DH, that the stress state is normal.

Next, if data analyzer 111 obtains the biological data for one day (step S403: YES), data analyzer 111 proceeds the process to step S404, and if data analyzer 111 does not yet obtain the biological data for one day (step S403: NO), data analyzer 111 returns the process back to step S401 and obtains the biological data to be measured next.

In this process, when it becomes "00:00", data analyzer 111 may determine YES in step S403 and deal with the biological data for one day obtained on the previous day, as the biological data for an object day that is to be processed.

Next, data analyzer 111 extracts the biological data of the concerning user for the object day from biological data table T4 and counts abnormalities in the extracted biological data (step S404). In this process, data analyzer 111 may count the number of pieces of the biological data in which "abnormal" is written in the "determination result" field, of the biological data of the concerning user for the object day, in biological data table T4.

Next, data analyzer 111 determines whether stress has a tendency to increase, by comparing the count value of abnormalities for the object day to the count values of abnormalities for a certain number of past days (step S405). Suppose, for example, the certain number of past days are two days. In addition, the count value of abnormalities for each day is assumed to be E. In this case, data analyzer 111 may determine that there is an increasing tendency, for example, if $\Delta E1 = E$ (object day)$-E$ (previous day)$>$a reference differential value and if $\Delta E2 = E$ (previous day)$-E$ (two days before)$>$the reference differential value. On the other hand, data analyzer 111 may determine that there is no increasing tendency if $\Delta E1 = E$ (object day)$-E$ (previous day)$\leq$the reference differential value. As the reference differential value, an integer more than or equal to 1 can be used, for example. Alternatively, in order to eliminate a case where the count value increases due to a measurement error or the like, an integer greater than or equal to 2 may be used as the reference differential value. In this case, a period of two days is taken as an example of the certain number of past days, but this is just an example, and one day or three days and more may be used.

Next, if stress has a tendency to increase (step S406: YES), data analyzer 111 transmits, by using communication unit 13, the information related to stress to user terminal 2 in association with the access acceptability request and, at the same time, transmits the information related to stress to business operator terminal 5 (step S407). As the timing when information related to stress is transmitted, a predetermined time (for example, 7:00) in the next morning may be used, for example.

On the other hand, if stress does not have a tendency to increase (step S406: NO), data analyzer 111 does not transmit the information related to stress (step S410), and returns the process back to step S401.

Next, communication unit 13 receives the decision result of access acceptability from user terminal 2 (step S408). Next, communication unit 13 transmits the decision result of access acceptability to business operator terminal 5 (step S409). When the process in step S409 is finished, the process goes back to step S401.

By the above process, it is determined whether there is an increasing tendency in the frequency with which stress exceeds the normal range.

(Information Related to Stress)

Regarding the information related to stress, in a period from when the user was first determined to be in a stress state to when the information related to stress is output for a predetermined number-th time, the information related to stress is output to indicate that the stress accumulated in the user is in a state where the stress needs to be paid attention to. Further, when the information related to stress is output the next time after the information related to stress is output the predetermined number of times, the information indicating that the stress of the user exceeds the predetermined normal range is output. As described above, notification intensity of the information related to stress is changed in a step-by-step manner.

Figure 16:
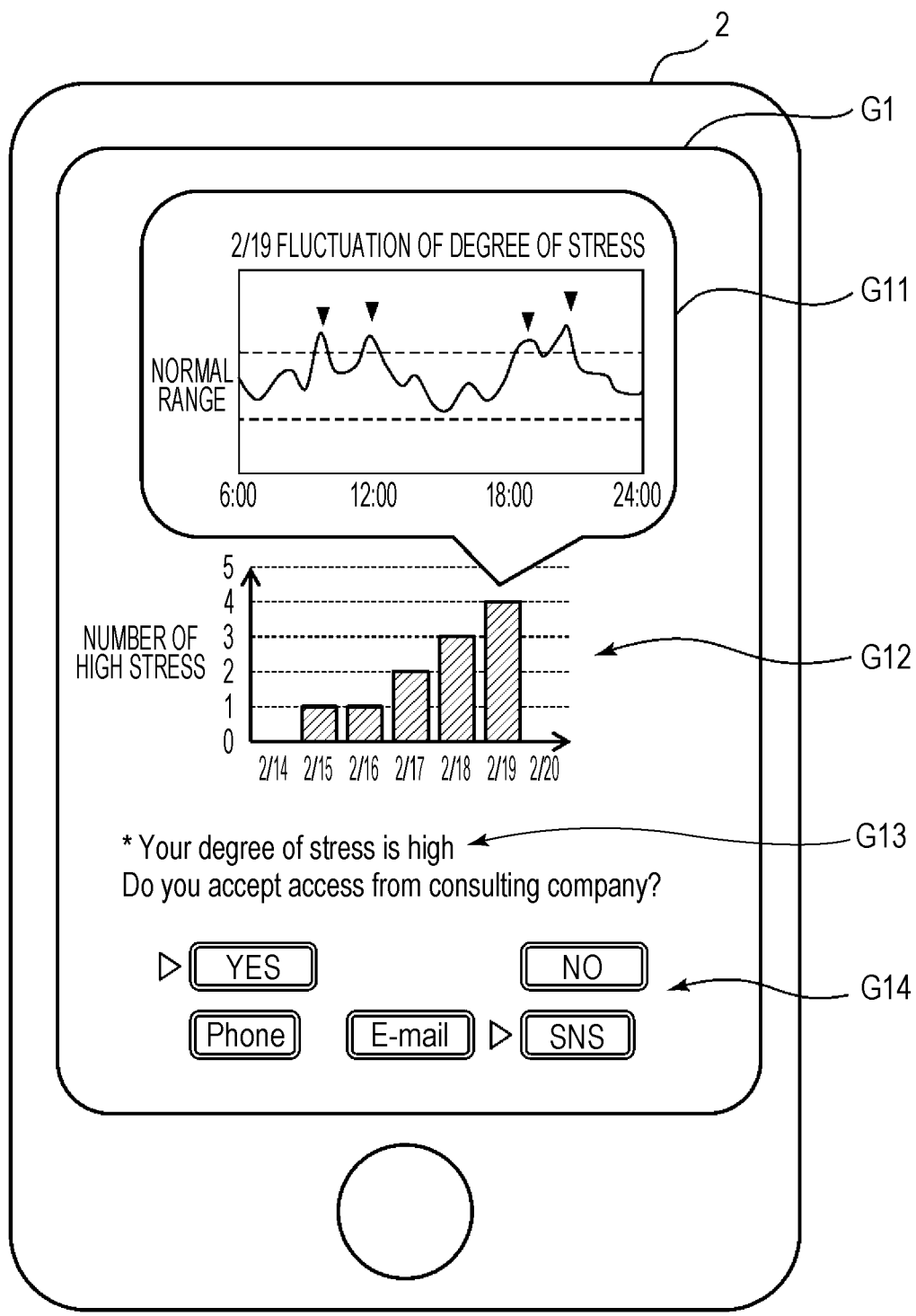
FIG. 16 is a diagram showing an example of a display screen displayed on a user terminal as information related to stress.

FIG. 16 is a diagram showing an example of display screen G1 displayed on user terminal 2 as the information related to stress. Display screen G1 includes graph G11, graph G12, message display field G13, and input field G14.

Graph G12 shows a relationship between a number of high-stress cases for the object day (in this case, February 19th) and numbers of high-stress cases for the certain number of past days (in this case, five consecutive days from February 14th to February 18th). In graph G12, the number of high-stress cases represents how many times the biological gas concentration exceeded the normal range. In the example of graph G12, because the number of high-stress cases has a tendency to increase from February 16th to February 19th, the stress is determined to have a tendency to increase, and display screen G1 is displayed on user terminal 2.

Graph G11 shows how the degree of stress temporally transits in a predetermined period (in this case, from 6:00 to 24:00) for a day for which the stress is determined to have a tendency to increase (in this case, February 19th). The degree of stress shown in graph G11 corresponds to the biological gas concentration. In graph G11, the triangular markers are displayed at the points at which the degree of stress exceeds the upper limit of the normal range so that the user can easily recognize where the stress is high.

Here, user terminal 2 may be configured as follows: if user terminal 2 detects an operation, on graph G12, of the user choosing a desired day, user terminal 2 displays graph G11 for the chosen day on display screen G1. This configuration enables the user to look back her life in the past several days and to know the reason (stressor) why the stress becomes high.

Note that graphs G11 and G12 are examples of the information indicating that the stress of the user exceeds the predetermined normal range.

In message display field G13, there is displayed a message notifying the user that the stress is high. In this case, the displayed message says "Your degree of stress is high". Since display screen G1 of FIG. 16 is the output in the period from when the user was first determined to be in a stress state to when display screen G1 is output for the predetermined number-th time, message display field G13 displays "Your degree of stress is high". This message is an example of the information indicating that the stress accumulated in the user is in a state where the stress needs to be paid attention to. Note that at the following times after the predetermined number-th time, in message display field G13 there is displayed information indicating that the stress of the user exceeds the predetermined normal range. In this case, in message display field G13, there is displayed a message saying, for example, "Be careful. Your stress exceeds predetermined normal range".

Input field G14 is a field for the user to input the decision result whether to accept access or not. In input field G14, there are displayed a message saying "Do you accept access from consulting company?", a "YES" button, a "NO" button, a "Phone" button, an "E-mail" button, and an "SNS" button. The consulting company is the aforementioned consulting business operator.

The "YES" button is used by the user to set the access acceptability to "permission". The "NO" button is used by the user to set the access acceptability to "prohibition". If the user chooses the "YES" button, a triangular cursor is displayed on the left side of the "YES" button. If the user chooses the "NO" button, a triangular cursor is displayed on the left side of the "NO" button. The above display enables the user to easily know which button is chosen.

If the user chooses the "YES" button, the decision result that the access acceptability is "permission" is transmitted from user terminal 2 to server 1, and if the user chooses the "NO" button, the decision result that the access acceptability is "prohibition" is transmitted from user terminal 2 to business operator terminal 5 via server 1.

The "Phone" button is used by the user to permit an access by telephone. The "E-mail" button is used by the user to permit an access by e-mail. The "SNS" button is used by the user to permit an access by SNS. If the user chooses any one of the "Phone" button, "E-mail" button, and the "SNS" button, a triangular cursor is displayed on the left side of the chosen button. The above display enables the user to easily know which button is chosen.

If the user chooses any one of the "Phone" button, the "E-mail" button, and "SNS" button, the result of the choice is transmitted from user terminal 2 to business operator terminal 5 via server 1. Therefore, regarding the user who permits the access acceptability, the representative of the consulting business operator accesses the user by using the access method corresponding to the button chosen by the user.

In the aspect described in this case, the user chooses any one of phone, e-mail, and SNS; however, the present disclosure is not limited to this aspect, and an aspect may be employed in which the user can choose any one or more of telephone, e-mail, and SNS. Note that input field G14 is an example of display information that makes the user choose whether the user accepts an access from the consulting business operator to the user.

Figure 17:
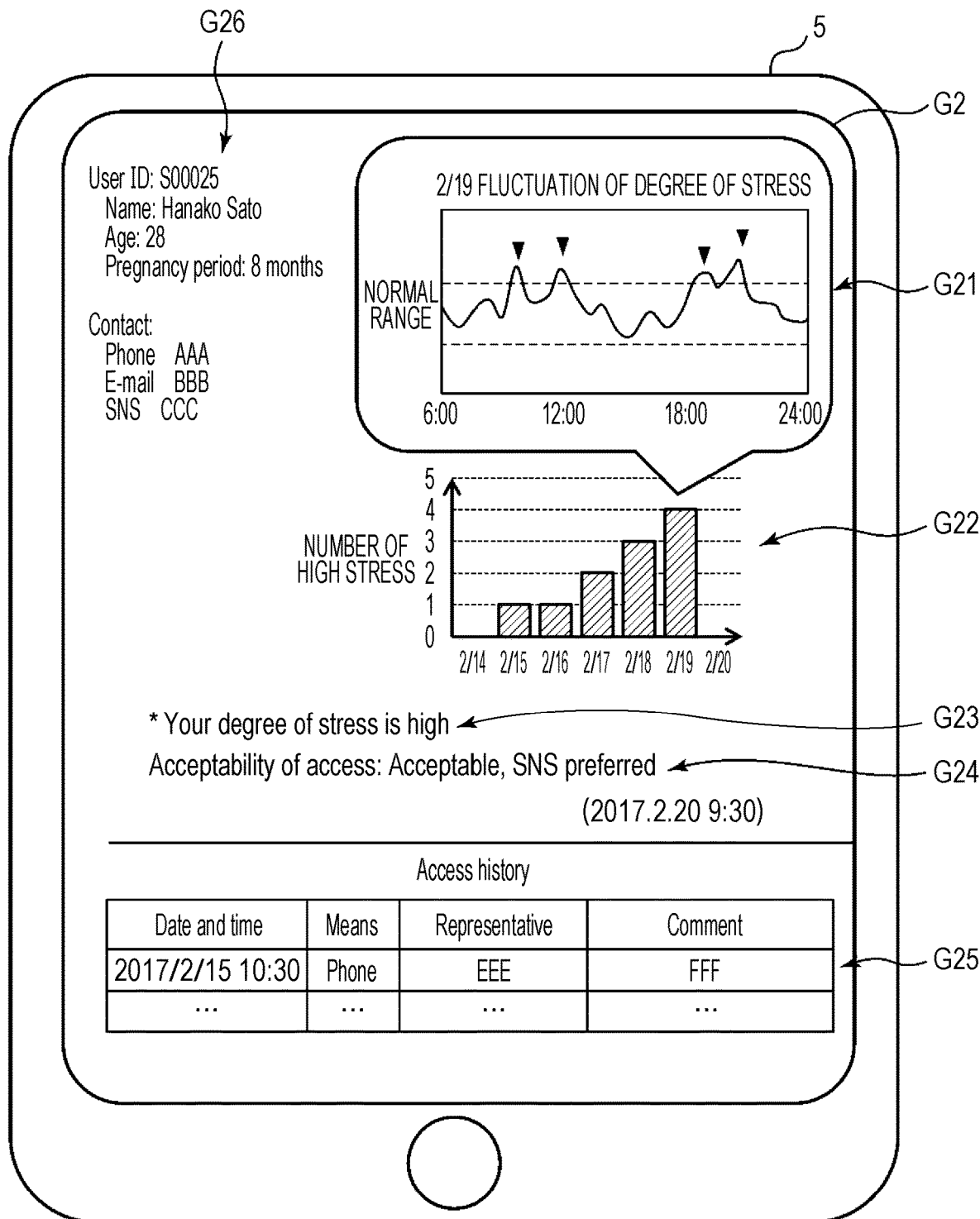
FIG. 17 is a diagram showing an example of a display screen displayed on a business operator terminal as the information related to stress.

FIG. 17 is a diagram showing an example of display screen G2 displayed on business operator terminal 5 as the information related to stress. Display screen G2 includes graph G21, graph G22, message display field G23, access acceptability display field G24, access history display field G25, and user information display field G26.

Graph G21, graph G22, and message display field G23 are the same as graph G11, graph G12, and message display field G13 of FIG. 16.

In access acceptability display field G24, there are displayed the decision result of the access acceptability and the access method chosen by the concerning user. In this case, the user chooses "permission" as the decision result of the access acceptability and chooses "SNS" as the access method. Therefore, in access acceptability display field G24, there is displayed "Access acceptability: Acceptable, SNS preferred". This display enables the user to determine whether the user can access the concerning user. In addition, in access acceptability display field G24, there is written "2017.2.20 9:30", and is also displayed the time when the user input the decision result of the access acceptability.

In access history display field G25, there is displayed the history of the representative accessing the concerning user. Regarding access history display field G25, one access is assigned to one row, and access history display field G25 includes a "date and time" column, a "means" column, a "representative" column, and a "comment" column. In the "date and time" column, there is displayed the date and time when the representative accessed the user; in the "method" column, there is displayed an access method (for example, telephone); in the "representative" column, there is displayed the name of the representative having accessed the user; and in the "comment" column, there is displayed the comment of the representative. In the "comment" column, there is written, for example, an impression and the like that the representative had on the user. For example, in the "comment" column there is written a comment meaning that the user actively answered the questions from the representative.

Note that the access history shown in access history display field G25 is compiled in a data base, for example, on business operator server 4, and business operator terminal 5 may display the access history by using the data base.

In user information display field G26, there is displayed the user information of an access object user. In this case, in user information display field G26, there are displayed "user ID", "name", "pregnancy period", and "contact information". These pieces of information are compiled in a data base and are managed by server 1. Note that this data base may be included in user information table T1 shown in FIG. 12. In this case, user information table T1 shown in FIG. 12 may be added with "name" and "pregnancy period".

In the example of FIG. 17, since "Access permitted, SNS preferred" is written in access acceptability display field G24, the representative will communicate with the user by accessing the contact information of the SNS in user information display field G26 by using business operator terminal 5.

As described above, since in display screen G2 there are displayed the user information of the access object user and, in addition, a fluctuation pattern of the degree of stress, and a fluctuation tendency of the number of high-stress cases, the representative can smoothly communicate while grasping a personal image and the degree of stress of the access object user.

(Schedule Information)

Here, display screens G1 and G2 respectively shown in FIGS. 16 and 17 may display schedule information of the concerning user. In this case, server 1 may include a data base that manages the schedule information of the user.

The data base managing the schedule information stores, for example, pieces of information such as "user ID", "schedule", and "date and time" in association with each other. "Schedule" is a schedule of the user (for example, "conference" and the like), and is input by the user via, for example, user terminal 2. "Date and time" is a scheduled date and time when the schedule written in "schedule" is to be done and is input by the user via user terminal 2.

When transmitting the information related to stress, server 1 transmits the schedule information of the concerning user for the certain number of past days to user terminal 2 and business operator terminal 5 by embedding the schedule information in the information related to stress.

User terminal 2 and business operator terminal 5 may generate display screens G1 and G2 by using the schedule information. As a display form of the schedule information, a form can be employed in which the schedule information of the user is displayed in graphs G11 and G21 in association with the time slot. For example, a form may be employed in which the schedule of the user is displayed in association with the time shown on graphs G11 and G21. This display enables the user to easily check the causation between stress and behaviors of the user herself.

As described above, since the first embodiment objectively determines a stress amount by using concentration of heptadecane that has a correlation with the stress amount, it is possible to objectively determine a sign of postpartum depression without being affected by a subjective view of an expectant woman. Then, if there is an increasing tendency in a frequency with which the concentration of heptadecane exceeds the normal range, the information related to stress is transmitted to user terminal 2. Therefore, the expectant woman herself can objectively know, during a pregnancy period, a sign of postpartum depression, and prevention of postpartum depression can be therefore expected. Further, in this case, since the information related to stress is transmitted to business operator terminal 5, the representative can also objectively determine a sign of postpartum depression of the user, and it is expected that the stress of the user can be reduced through communication between the representative and the user and that postpartum depression can be thus prevented.

Second Embodiment

Figure 18:
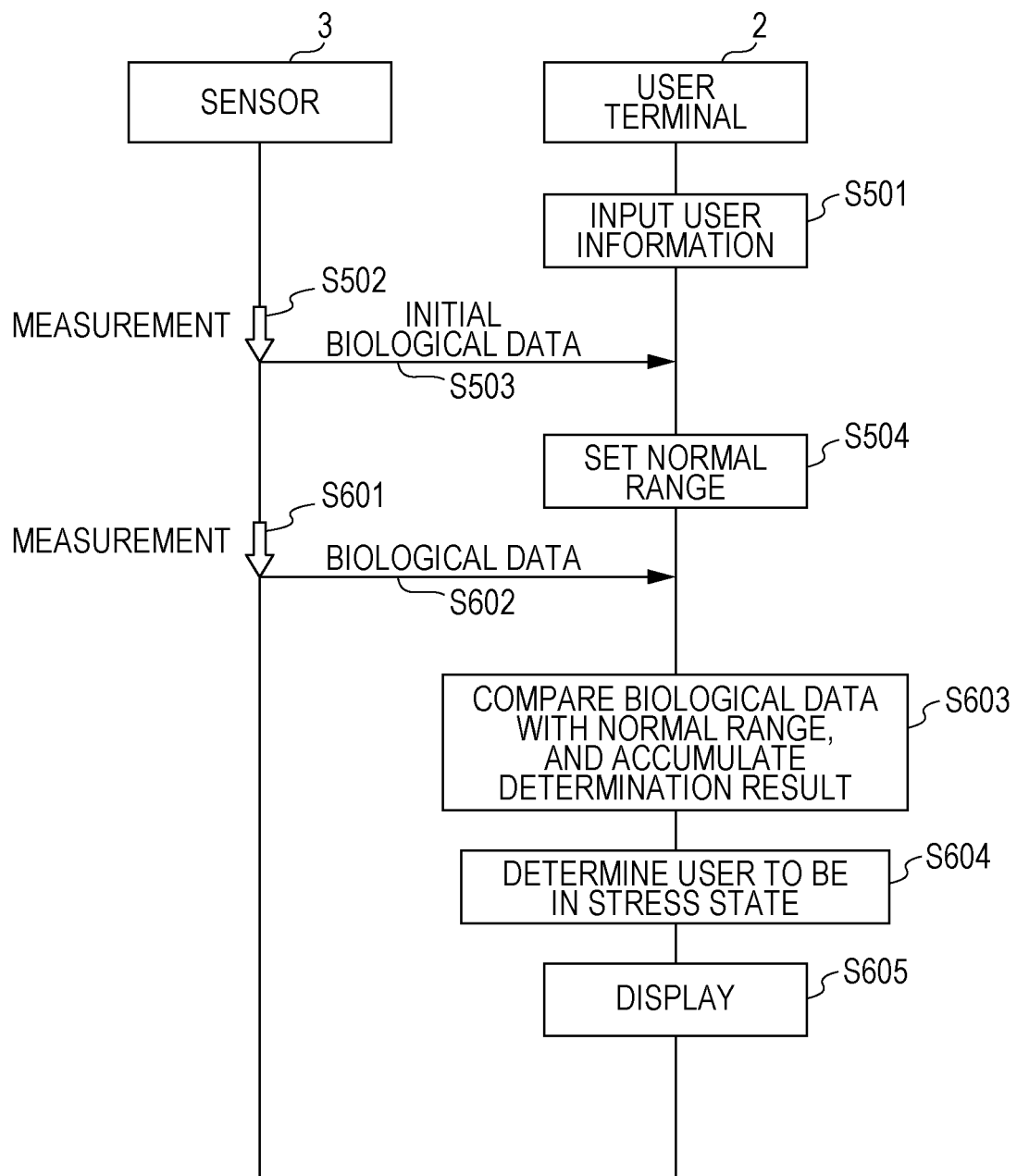
FIG. 18 is a sequence diagram showing a process in an information processing system according to a second embodiment of the present disclosure.

In a second embodiment, the functions of server 1 are incorporated in user terminal 2. Note that in the second embodiment, the same components as in the first embodiment are assigned the same reference signs and are not described again. FIG. 18 is a sequence diagram showing a process in an information processing system according to the second embodiment of the present disclosure.

In FIG. 18, the difference from FIG. 13 is that server 1 and business operator terminal 5 are omitted and that information processing system is configured with sensor 3 and user terminal 2. Steps S501 to S504 correspond to the initial phase.

Steps S501, S502, and S503 are the same as steps S101, S103, and S104 in FIG. 13. Step S504 is the same as step S106 in FIG. 13 except that step S504 is performed not on server 1 but on user terminal 2.

Steps S601 to S605 correspond to the normal phase. Steps S601 and S602 are the same as steps S201 and S202 in FIG. 13. Steps S603 and S604 are the same as steps S204 and S205 in FIG. 13 except that steps S603 and S604 are performed not on server 1 but on user terminal 2.

In step S605, controller 21 of user terminal 2 causes display unit 23 to display information related to stress.

Note that step S502 is shown only once in the example of FIG. 18 but is performed for a plurality of times to obtain necessary pieces of biological data to calculate the normal range. Note that step S601 is shown only once but is performed for a plurality of times to determine that there is an increasing tendency in a frequency with which the biological gas concentration exceeds the upper limit of the normal range.

As described above, with the information processing system according to the second embodiment, also in the aspect in which the functions of server 1 are incorporated in user terminal 2, postpartum depression can be prevented similarly to the first embodiment.

In the present disclosure, the following variations can be employed.

(1) In the above description, the information related to stress is transmitted to user terminal 2 and business operator terminal 5, but in the present disclosure, the information related to stress only has to be transmitted to one of user terminal 2 and business operator terminal 5 on the other hand.

Figure 19:
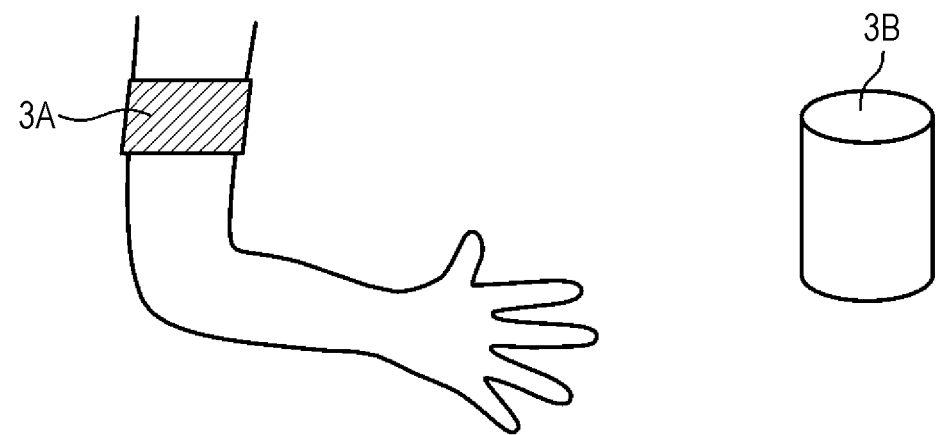
FIG. 19 is a diagram showing an example of a sensor according to a variation of the present disclosure.

(2) In the above description, sensor 3 is integrally configured, but the present disclosure is not limited to the above configuration. FIG. 19 is a diagram showing an example of sensor 3 according to a variation of the present disclosure. Regarding sensor 3 according to the variation, wearable part 3A to be mounted on a user and main body part 3B are separately configured. Wearable part 3A is configured with a fitting belt that is detachable to the arm at a point near the underarm of the user. Wearable part 3A is attached with an absorbent for absorbing a biological gas.

Wearable part 3A is configured to be detachable also to main body part 3B. Main body part 3B includes detection unit 33, controller 31, and communication unit 34 shown in FIG. 7. When wearable part 3A is attached to main body part 3B, main body part 3B heats the absorbent with, for example, a heater to desorb the biological gas from the absorbent, analyzes the biological gas, extracts a measurement object biological gas (heptadecane in this embodiment), and measures a biological gas concentration. Then, main body part 3B transmits the biological data including the measured biological gas concentration to user terminal 2. In this variation, wearable part 3A is made compact, and a user's burden can be thus reduced.

(3) The second embodiment can be applied to, for example, a case where the user receives a diagnosis from a doctor at a hospital. In this case, a computer of the doctor who makes a diagnosis of the user is used as user terminal 2.

In this case, for example, the user visits the hospital on a regular basis (for example, once a week, once in two weeks, once a month, or the like), and the user is instructed by the doctor to wear sensor 3 for a specific period (for example, one, two, or three days) immediately before visiting the hospital. Sensor 3 stores the biological data measured in this specific period in memory 32 in association with the measurement time. Memory 32 is a memory detachable to sensor 3.

User brings memory 32 to the hospital when visiting the hospital. Doctor connects this memory 32 to user terminal 2 to cause user terminal 2 to acquire the biological data obtained in this specific period. Then, user terminal 2 determines, based on the acquired biological data, whether there is an increasing tendency in the number of times when the biological gas concentration exceeded the normal range, and user terminal 2 causes display unit 23 to display the information related to stress. On the other hand, if user terminal 2 determines that there is no increasing tendency, user terminal 2 does not cause display unit 23 to display the information related to stress. In this case, user terminal 2 may cause display unit 23 to display, for example, information indicating that stress of the user is normal. This variation can provide a doctor who makes a diagnosis of conditions of an expectant woman, with data useful to prevent postpartum depression.

INDUSTRIAL APPLICABILITY

The present disclosure is expected to prevent postpartum depression and is therefore useful for an information processing system that manages stress of a user.

REFERENCE SIGNS LIST

1 server
2 user terminal
3 sensor
4 business operator server
5 business operator terminal
11 controller
12 memory
13 communication unit
21 controller
22 memory
23 display unit
24 communication unit
31 controller
32 memory
33 detection unit
34 communication unit
41 controller
42 memory
43 communication unit
51 controller
52 memory
53 display unit
54 communication unit
111 data analyzer
NT network
T1 user information table
T2 normal range data table
T3 business operator information table
T4 biological data table
U1 user

The invention claimed is:

1. A method for providing information in an information processing system, the method comprising:
   acquiring, via a network, biological gas information representing a concentration of heptadecane of a user detected with a sensor for detecting heptadecane released from a skin surface of the user;
   obtaining reference information representing an upper limit of a normal range of the concentration of heptadecane per unit period of time, using a memory storing the reference information representing the upper limit of the normal range; and
   outputting information related to stress of the user to an information terminal after it is determined that a frequency with which the concentration of the heptadecane of the user per unit period of time is more than the upper limit of the normal range tends to increase, based on the biological gas information acquired in a pregnancy period of the user.

2. The method according to claim 1, wherein
   the information including the upper limit of the normal range of the concentration of heptadecane per the unit period is set for the user as individual information of the user, based on the biological gas information acquired in in a predetermined period in an early stage of the pregnancy period of the user.

3. The method according to claim 1, wherein
   the information including the upper limit of the normal range of the concentration of heptadecane per unit period is used commonly to a plurality of users including the user.

4. The method in an information processing system according to claim 1, wherein
   when it is not determined that the frequency with which the concentration of the heptadecane of the user per unit period of time is more than the upper limit of the normal range tends to increase, the information related to stress of the user is not output to the information terminal.

5. The method according to claim 1, wherein
   the information terminal is a first information terminal of the user.

6. The method according to claim 5, wherein
   the information terminal is a second information terminal, of a consulting business operator other than the first information terminal of the user.

7. The method according to claim 1, wherein
   the information terminal is a first information terminal of the user, and
   the method further includes:
   acquiring first address information on the first information terminal and second address information on a consulting business operator from a memory storing the first address information and the second address information, when it is determined that the frequency that the concentration of heptadecane of the user per the unit period of time is more than the upper limit of the normal range of tends to increase; and
   outputting the information related to stress of the user to both of the first information terminal and a second information terminal of the consulting business operator, based on the first address information and the second address information, wherein the second information terminal of the consulting business operator is distinct form the first information terminal.

8. The method according to claim 7, wherein
the information to be output to the first information terminal includes display information for allowing the user to select whether to accept contact of the consulting business operator with the user.

9. The method according to claim 1, wherein
the information related to the stress of the user is used to call the user's attention to a need for reducing stress build up in the user.

10. The method according to claim 1, wherein
the information related to the stress of the user indicates that the stress of the user is more than the predetermined normal range.

11. The method according to claim 1, wherein
the sensor for detecting heptadecane is built in a device to be worn on the user.

12. The method according to claim 1, wherein
the information processing system is configured to acquire the biogas information along with a user ID of the user, and to output the information related to stress on the user to the information terminal associated with the user ID of the user.

13. An information processing system comprising:
a server device; and
an information terminal,
wherein the server device is configured to:
  acquire biological gas information presenting a concentration of heptadecane of a user acquired by a sensor that detects heptadecane discharged from a skin surface of the user,
  obtain reference information representing an upper limit of a normal range of the concentration of heptadecane per unit period of time, using a memory storing the reference information representing the upper limit of the normal range, and
  output information related to stress of the user to the information terminal after it is determined that a frequency that the concentration of heptadecane of the user per the unit period of time is more than the upper limit of the normal range tends to increase, based on the biological gas information acquired in a pregnancy period of the user, and
wherein the information terminal displays the information related to stress of the user on the display of the information terminal.

14. An information terminal comprising:
a display operatively connected to a server device,
wherein the server device is configured to:
  acquire biological gas information presenting a concentration of heptadecane of a user acquired by a sensor that detects heptadecane discharged from a skin surface of the user,
  obtain reference information representing an upper limit of a normal range of the concentration of heptadecane per unit period of time, using a memory storing the reference information representing the upper limit of the normal range, and
  output information related to stress of the user to the information terminal after it is determined that a frequency that the concentration of heptadecane of the user per the unit period of time is more than the upper limit of the normal range tends to increase, based on the biological gas information acquired in a pregnancy period of the user, and
wherein the display displays the information related to stress of the user.

15. An information processing method using a computer, the method comprising:
  acquiring, via a network, biological gas information representing a concentration of heptadecane of a user acquired by a sensor that detects heptadecane discharged from a skin surface of the user;
  obtaining reference information representing an upper limit of a normal range of the concentration of heptadecane per unit period of time, using a memory storing the reference information representing the upper limit of the normal range; and
  outputting information related to stress of the user to display on a display the information related to stress of the user after it is determined a frequency that the concentration of heptadecane of the user per the unit period of time is more than the upper limit of the normal range tends to increase, based on the biological gas information acquired in a pregnancy period of the user.

16. The method according to claim 15, wherein
the display is provided in an information terminal of the user.

17. The method according to claim 15, wherein
the information related to stress of the user is used to call the user's attention to a need for reducing stress build up in the user.

18. The method according to claim 15, wherein
the information related to stress of the user indicates that stress build up in the user is more than a predetermined normal range.

* * * * *